United States Patent [19]

Peglion et al.

[11] Patent Number: 5,189,045
[45] Date of Patent: Feb. 23, 1993

[54] AMINOPIPERIDINE INDANYL AND BENZOCYCLOBUTENE COMPOUNDS

[75] Inventors: Jean-Louis Peglion; Francis Colpaert, both of Le Vesinet, France

[73] Assignee: Adir et Compagnie, Courbevoie, France

[21] Appl. No.: 702,591

[22] Filed: May 17, 1991

[30] Foreign Application Priority Data

May 18, 1990 [FR] France .................... 90 06220

[51] Int. Cl.$^5$ .................... C07D 413/06; A61K 31/00
[52] U.S. Cl. .................... 514/319; 546/205; 546/206
[58] Field of Search ............... 546/205, 206; 514/319

[56] References Cited

U.S. PATENT DOCUMENTS 2,628,973  2/1953  Cusic ........................... 546/206
3,549,645 12/1970  Heerdt ......................... 546/206

OTHER PUBLICATIONS

CA108: 21530m 1991 (Abstract of PCT WO 8702035 Apr. 9, 1987 and GB 85-24491 Oct. 4, 1985, GB 86-15560 Jun. 25, 1986).

Primary Examiner—Marianne M. Cintins
Assistant Examiner—Catherine S. Kilby Scalzo
Attorney, Agent, or Firm—Gordon W. Hueschen

[57] ABSTRACT

The invention relates to new compounds of formula I:

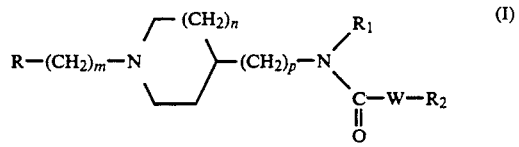

in which:
m represents zero, 1, 2, 3 or 4,
n and p represent zero, 1 or 2,
W represents an oxygen atom, an —NH— radical, or a single bond,
R represents a benzocyclobuten-1-yl radical, or an indanyl radical, a 2,3-dihydrobenzofuran-2-yl
$R_1$ represents a hydrogen atom, an alkyl radical having from 1 to 6 carbon atoms, or an aryl radical, and
$R_2$ represents a hydrogen atom, an alkyl radical, an alkenyl radical, a cycloalkyl radical, a benzyl radical, a phenyl radical, an aralkyl radical, an alkoxyalkyl radical or a polyhalogenated alkyl radical, the optical isomers thereof and the addition salts thereof with a pharmaceutically acceptable organic or mineral acid, and medicaments containing the same.

15 Claims, No Drawings

AMINOPIPERIDINE INDANYL AND BENZOCYCLOBUTENE COMPOUNDS

The present invention relates to new aminopiperidine, aminopyrrolidine and aminoperhydroazeopine compounds, to processes for the preparation thereof, and to pharmaceutical compositions containing them.

Certain 4-benzoylamino-1-cycloalkenylmethylpiperidine compounds having dopamine antagonistic activity and serotonin receptor-stimulating activity are described in patent Application FR-2 369 263. The Applications EP-160 422, EP-256 798 and EP-277 794 describe N-aryl-N-(4-piperidyl)-amides having analgesic, anaesthetic and sedative properties.

The Application FR-2 370 731 describes amides derived from piperidine that have the ability to neutralise the effects of dopamine or dopaminergic agents.

Certain amides derived from pyridine, tetrahydropyridine and piperidine that have hypotensive, anti-inflammatory and analgesic activity are described in GB-1410783, and certain N-aryl-N-piperidylarylacetamides having anti-arrhythmia properties are described in Patent Application FR-2 325 377.

The compounds of the invention are distinguished from other piperdine, pyrrolidine and perhydroazepine compounds described in the literature by their novel structures and their pharmacological properties. Pharmacological tests have shown that the compounds of the invention are 5-HT$_{1A}$ receptor antagonists. Some of them also have a good affinity to the sigma receptor. The compounds of the invention can therefore be used to treat pain, stress, migraine, anxiety, depression and schizophrenia.

The present invention relates more especially to compounds of formula I:

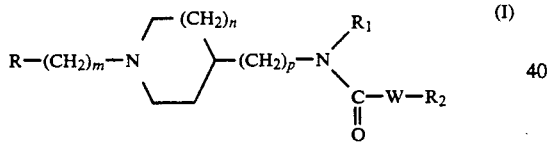

in which:
m represents zero, 1, 2, 3 or 4,
n and p represent zero, 1 or 2,
W represents an oxygen atom, an —NH— radical, or a single bond,
R represents
a 1,2-dihydro-2-oxo-1-phenyl-1,8-naphthyridin-3-yl radical of formula A

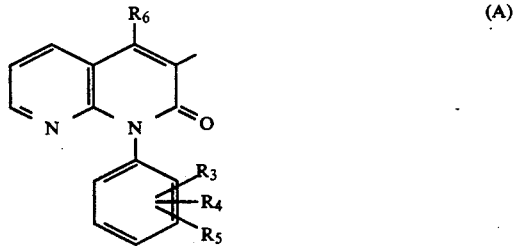

(in which $R_3$, $R_4$ and $R_5$, which may be the same or different, each represents a hydrogen atom, a halogen atom, an alkyl or alkoxy radical having from 1 to 6 carbon atoms, a hydroxy radical, a polyhalogenated alkyl radical having from 1 to 6 carbon atoms, or an alkylthio radical having from 1 to 6 carbon atoms, and $R_6$ represents a hydrogen atom or a hydroxy radical), a benzocyclobuten-1-yl radical of formula B:

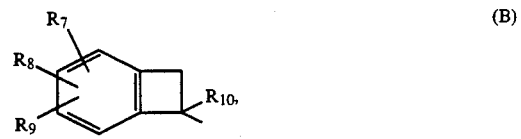

an indanyl radical of formula C:

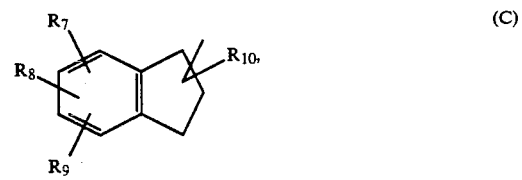

a 2,3-dihydrobenzofuran-2-yl radical of formula E:

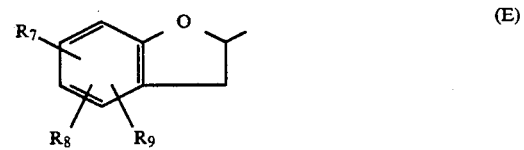

or a 4-oxo-4H-chromen-2-yl radical of formula F:

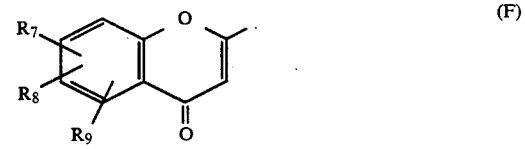

(in which:
$R_7$, $R_8$ and $R_9$, which may be the same or different, each represents a hydrogen atom, a halogen atom, an alkyl or alkoxy radical having from 1 to 6 carbon atoms, a polyhalogenated alkyl radical having from 1 to 6 carbon atoms, or a hydroxy radical, or $R_7$ and $R_8$ or $R_8$ and $R_9$ together form a methylenedioxy radical, an ethylenedioxy radical, a furan ring or a dihydrofuran ring and
$R_{10}$ represents a hydrogen atom or an alkyl radical having from 1 to 6 carbon atoms);
$R_1$ represents a hydrogen atom or an alkyl radical having from 1 to 6 carbon atoms, or an aryl radical, with the proviso, however, that when, simultaneously, R represents an indanyl radical, p represents zero and W represents a single bond, $R_1$ does not represent an aryl radical;
$R_2$ represents a hydrogen atom, an alkyl radical having from 1 to 6 carbon atoms, an alkenyl radical having from 2 to 6 carbon atoms, a cycloalkyl radical having from 4 to 7 carbon atoms, a benzyl radical or a phenyl radical (each optionally substituted by one or more halogen atoms, hydroxy radicals, or alkyl or alkoxy radicals having from 1 to 6 carbon atoms), an aralkyl radical having from 7 to 12 carbon atoms, an alkoxyalkyl radical having from 2 to 7 carbon atoms or a polyhalogenated alkyl radical having from 1 to 6 carbon atoms, the optical isomers thereof and the addition salts thereof with a pharmaceutically acceptable organic or mineral acid.

The present invention also relates to a process for the preparation of compounds of the general formula I, characterised in that:

a) a compound of formula II $$R-(CH_2)_m-X \quad \text{(II)}$$

in which R and m are as defined for formula I, and X represents a halogen atom, a tosyloxy radical or a mesyloxy radical, is condensed with a compound of formula III:

<chemical structure (III): HN<(CH_2)_n / (CH_2)_p >—N(R_1)—C(=O)—W—R_2> in which n, p, $R_1$, W and $R_2$ are as defined for formula I, to yield compounds of formula I, b) or a compound of formula IV:

<chemical structure (IV): R_7, R_8, R_9 substituted benzene with (CH_2)_q, (CH_2)_s connecting to X bearing R_{10} and (CH_2)_{m'-1}—COOH> in which $R_7$, $R_8$, $R_9$ and $R_{10}$ are as defined above, m' represents 1, 2, 3 or 4, and q and s each represent 0, 1 or 2, with the proviso, however, that q+s is equal to 1 or 2, is reacted with a compound of formula V:

<chemical structure (V): H—N<(CH_2)_n / (CH_2)_p>—N(R_1)(CH_2-phenyl)> in which n, p and $R_1$ are as defined for formula I, to yield a compound of formula VI:

in which $R_1$, $R_7$, $R_8$, $R_9$, $R_{10}$, m', n, p, q and s are as defined above, which is subjected to the action of hydrogen in the presence of a catalyst such as $PtO_2$ or Rd/C, in an alcoholic solvent, in the presence of a stoichiometric amount of hydrochloric or acetic acid, to yield a compound of formula VIII:

<chemical structure (VIII)> in which $R_1$, $R_7$, $R_8$, $R_9$, $R_{10}$, m', n, p, g and s are as defined above, which is then α) reacted with a compound of formula IX:

$$Cl-C(=O)-W-R_2 \quad \text{(IX)}$$

in which $R_2$ is as defined for formula I but does not represent a hydrogen atom, and W represents a single bond or an oxygen atom, to yield compounds of formula I in which R represents a radical B or a radical C, W represents a single bond or an oxygen atom, $R_2$ is as defined above but does not represent a hydrogen atom, and m is as defined above with the exception of zero, β) or reacted with formic acid in the presence of acetic anhydride to obtain compounds of formula I in which R represents a radical B or a radical C, W represents a single bond, $R_2$ represents a hydrogen atom, and m is as defined above with the exception of zero, γ) or reacted with a compound of formula X:

$$R_2-N=C=O \quad \text{(X)}$$

in which $R_2$ is as defined for formula I with the exception of a hydrogen atom, to yield compounds of formula I in which R represents a radical B or a radical C, W represents an —NH— radical, $R_2$ is as defined above with the exception of a hydrogen atom, and m is as defined above with the exception of zero, c) or a compound of formula XI:

(VI)

<chemical structure (VI)> in which $R_1$, $R_7$, $R_8$, $R_9$, $R_{10}$, n, p, q and s are as defined above, and m' represents 1, 2, 3 or 4, which is subjected to the action of lithium aluminium hydride to yield a compound of formula VII:

(VII)

<chemical structure (VII)>

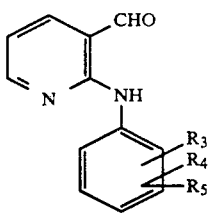

in which $R_3$, $R_4$ and $R_5$ are as defined for formula A, is reacted, in the presence of sodium hydride, with a compound of formula XII:

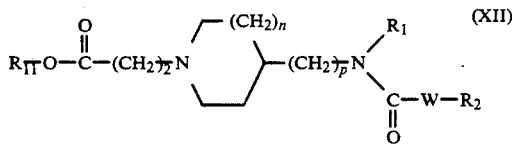

in which n, p, $R_1$, $R_2$ and W are as defined for formula I and $R_{11}$ represents an alkyl radical having from 1 to 3 carbon atoms, to yield compounds of formula I in which R represents a radical of formula A, and m is 1, which compounds of formula I are then, if desired:

converted into salts with a pharmaceutically acceptable organic or mineral acid, or separated into their optical isomers and then converted into salts.

When R represents a radical of formula F, the compounds of formula II are prepared from 2-hydroxyacetophenone derivatives and ethyl 2-methylthioacetate (J. Org. Chem., (1984), 49, p. 5038).

When R represents a radical of formula E, the compounds of formula II are prepared from suitable (2,3-dihydrobenzofuran-2-yl)-carboxylic acid derivatives (Chim. Ther., (1973), 3, p. 259). These compounds are subjected to the action of lithium aluminium hydride to yield the corresponding alcohols which enable compounds of formula II to be obtained by conventional methods.

When R represents a radical B, the compounds of formula II are obtained from acids of formula XIII:

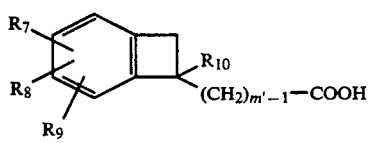

in which $R_7$, $R_8$, $R_9$ and $R_{10}$ are as defined above, and m' represents 1, 2, 3 or 4, in accordance with a process already described in the literature (J.A.C.S., (1975), 154, p. 347). Processes for the preparation of acids of formula XIII or their derivatives are also known (J.A.C.S., (1958), 80, p. 2257; J.A.C.S., (1975), 157, p. 347; J. Chem., (1972) 32, p. 820; J. Org. Chem., (1968), 33, p. 3327; Tet. Lett., (1973), 29, p. 73).

The piperidine compounds of formula $III_A$:

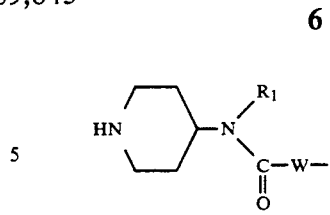

in which $R_1$ is as defined for formula I and W and $R_2$ are as defined for formula IX, may be prepared from 1-benzyl-4-oxopiperidine. That compound is subjected to the action of an amine of formula XIV:

$$H_2N-R_1 \quad (XIV)$$

in which $R_1$ is as defined formula I, then to the action of sodium borohydride dissolved in isopropanol, to yield compounds of formula XV:

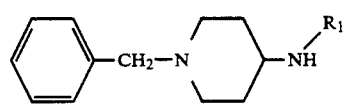

in which $R_1$ is as defined for formula I.

The compounds of formula XV are then subjected to the action of a compound of formula IX in the presence of triethanolamine in methylene chloride to yield compounds of formula XVI:

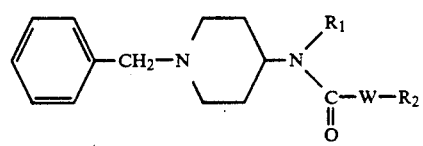

in which $R_1$ is as defined for formula I and W and $R_2$ are as defined for formula IX.

The latter compounds are then subjected to catalytic hydrogenation to yield the desired compounds.

The piperidine compounds of formula $V_A$:

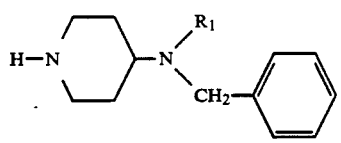

in which $R_1$ is as defined for formula I, are obtained from 1-acetyl-4-oxopiperidine. That compound is reacted with an amine of formula XVII:

$$H_2N-R_1 \quad (XVII)$$

in which $R_1$ is as defined for formula I, and then the reaction mixture is subjected to catalytic hydrogenation to yield compounds of formula XVIII:

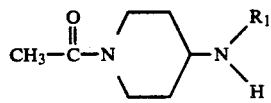

in which $R_1$ is as defined above.

The compounds of formula XVIII are then condensed with benzyl chloride in an alcohol, in the presence of sodium carbonate, to yield compounds of formula XIV:

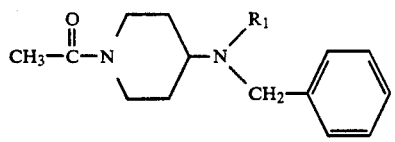

in which R₁ is as defined for formula I. The latter compounds are then subjected to the action of hydrochloric acid in methanol to yield compounds of formula $V_A$.

The compounds of formula XII are obtained by conventional methods (Michaäl reaction).

The optical isomers of compounds of formula I to which the present invention also relates can be obtained by conventional methods (conversion into salts with an optically active acid).

Among the pharmaceutically acceptable acids for the preparation of addition salts of compounds of the general formula I the following may be mentioned: phosphoric, hydrochloric, citric, hydriodic, oxalic, maleic, sulphuric, tartaric, mandelic, fumaric and methanesulphonic acid etc...

The compounds of the invention and the addition salts thereof exhibit very valuable pharmacological properties. Pharmacological tests have shown that the compounds of the invention behave like very powerful antagonists for 5-HT$_{1A}$ serotonin receptors, having an antagonistic activity in the central nervous system.

Moreover, some of them are good ligands for the sigma receptor.

The compounds of the invention are therefore used for the treatment of stress (Neuropharmac., (1989), Vol. 25, No. 5, p. 471–476), migraine (T.I.P.S., (1989), Vol. 10, pp. 200–204), anxiety, depression, schizophrenia and pain [Pharmacology and Toxicology, (1989), 64, p. 3–5; Drugs of the future, (1988), 13, No. 5, p. 429–437; J. Neurol. Transm., (1988), 74, p. 195–198].

The compounds, which are active with respect to 5-HT$_{1A}$ receptors, may also modify alimentary and sexual behaviour (J. of Receptor Research, (1988), 8, p. 59–81).

The pharmacological properties of sigma ligands are illustrated generally especially by: WALKER J. MICHAEL et al., Pharmacological Reviews (1990), 42 (4), 355–402, and in the field of analgesia by: Trends in Neurosci. (1987), 10, 444–446; Clin. Neuropharmacol. (1988), 11, 105 and Mol. Pharmacol. (1987), 32, 772–784.

The sigma ligands also serve to modulate the action of a variety of neurotransmitters—cf. Eur. J. Pharmacol. (1988), 149, 399–400.

1,3-ditolylguanidine and its derivatives have been used in the diagnosis and treatment of hallucinations associated with mental psychoses, cf. Trends in Neurosci. (1988), 11, 37–40.

The invention extends also to pharmaceutical compositions comprising as active ingredient at least one compound of the general formula I, or a salt thereof with a pharmaceutically acceptable organic or mineral acid, in association with one or more appropriate inert excipients.

The pharmaceutical compositions so obtained are advantageously presented in various forms, such as, for example, in the form of tablets, dragees, soft gelatin capsules, suppositories, and injectable or drinkable solutions.

The dosage can vary widely depending on age, the weight of the patient, the nature and severity of the disorder and the administration route. Generally, a single dose will range from 0.1 to 100 mg, and the daily dose for the treatment of humans from 0.1 to 500 mg. The preferred route of administration is the oral or parenteral route.

The following Examples, which are not limiting, illustrate the invention.

Melting points, unless specified otherwise, were measured according to the Micro-Kofler method.

The proton nuclear magnetic resonance spectra of the compounds of the general formula I were recorded at 200 or 400 MHz, as the case may be, and are indicated in Table I.

EXAMPLE 1

N-{1-[(4-oxo-4H-chromen-2-yl)-methyl]-piperid-4-yl)-N-methylpropionamide hydrochloride

Stage A 1-benzyl-4-methylaminopiperidine dihydrochloride

A freshly prepared solution of 15 g of monomethylamine in 45 ml of ethanol is poured onto 29.7 g of 1-benzyl-4-oxopiperidine in 340 ml of isopropanol that has been cooled to 5° C. and the mixture is left for 2 hours at 10° C.

10.5 g of sodium hydroxide solution are added and left for 1 hour at room temperature to dissolve. The mixture is adjusted to 10° C. and 8.1 g of sodium borohydride are added. The mixture is left overnight with stirring. The solvents are evaporated, the residue is taken up in water and extracted with ether, and the ethereal extract is dried over anhydrous sodium sulphate. This ethereal phase is filtered and then acidified with ethereal hydrogen chloride. The salt that precipitates is filtered off and dried to yield the desired product.

Yield: 77%

Melting point : >260° C.

Proton nuclear magnetic resonance spectrum (solvent D₂O): 7.55 ppm, 5H, s; 4.35 ppm, 2H, s; 3 to 3.09 ppm, 5H, m; 2.75 ppm, 3H; 1.5 to 2.6 ppm, 4H, m.

Stage B

N-(1-benzylpiperid-4-yl)-N-methylpropionamide 11 g of propionyl chloride are added dropwise to 33 g of the compound obtained in the above Stage in 300 ml of methylene chloride and 50.5 ml of triethylamine cooled to 5° C. the mixture is left at 0° C. for 1 hour, transferred to a flask, washed with water, dried and evaporated to yield the desired product.

Yield: 88%

Proton nuclear magnetic resonance spectrum (solvent CDCl₃): 7.3 ppm, 5H, s; 3.5 ppm, 2H, s; 3.3 to 2.8 ppm, 4H, m+s; 1.4 to 2.7 ppm, 10H, q+m+m; 1.1 ppm, 3H, t.

Stage C

N-piperid-4-yl-N-methylpropionamide 31 g of the amine obtained in Stage B are hydrogenated in 350 ml of ethanol with 1 g of palladium hydroxide at atmospheric pressure and room temperature. The mixture is filtered and evaporated to yield the desired product in the form of an oil.

9

Yield: 60%

Proton nuclear magnetic resonance spectrum (solvent CDCl$_3$): 3.5 to 2 ppm, 10H, p+s+m+gl+H exchangeable; 1.3 to 1.9 ppm, 4H, m; 1.1 ppm, 3H, t.

Stage D 6.3 g of (4-oxo-4H-chromen-2-yl)-methyl iodide, 3.7 g of the compound obtained in the above Stage, and 3 ml of triethylamine in 70 ml of dimethylformamide are heated at 60° C. for 4 hours with stirring. The solvent is then evaporated off, the residue taken up in diethyl ether and washed with iced water, and the ethereal solution dried and evaporated. The resulting oil is purified by flash chromatography using a mixture of ethyl acetate and methanol (95:5 v/v) as solvent.

Yield: 36%

2.5 g of the base obtained in this manner are dissolved in 5 ml of ethanol. 1.5 ml of 5N ethereal hydrogen chloride are added, the precipitate is filtered off and dried to yield N-(1-[(4-oxo-4H-chromen-2-yl)methyl]-piperid-4-yl)-N-methylpropionamide hydrochloride.

Yield: 72%

Melting point: 220°–222° C.

Elemental analysis:

|      | Theory | Found |
| ---- | ------ | ----- |
| C %  | 62.55  | 62.15 |
| H %  | 6.91   | 6.69  |
| N %  | 7.68   | 7.61  |
| Cl % | 9.72   | 9.52  |

EXAMPLE 2

N-{1-[(4-oxo-4H-chromen-2-yl)-methyl]-piperid-4-yl}-N-methylbutanamide

Stage A

N-(1-benzylpiperid-4-yl)-N-methylbutanamide

This compound was obtained from 1-benzyl-4-methylaminopiperidine dihydrochloride and butyryl chloride in accordance with the process described in Stage B of Example 1.

Yield: 82%

Proton nuclear magnetic resonance spectrum (solvent CDCl$_3$): 7.3 ppm, 5H, m; 4.6 ppm, 1H, m; 3.5 ppm, 2H, s; 3 ppm, 2H, t; 2.8 ppm 3H, s; 2.3 ppm, 2H, t; 1.7 ppm, 2H, m; 1.6 ppm, 3H, t; 1.5 to 2.3 ppm, 6H, m.

Stage B

N-piperid-4-yl-N-methylbutanamide

The compound was obtained from the compound described in the above Stage and in accordance with the process described in Stage C of Example 1. The hydrogenation was carried out at 40° C. under 40 Kg.

Yield: 64%

Proton nuclear magnetic resonance spectrum (solvent CDCl$_3$): 4.65 ppm, 1H, m; 3.2 ppm, 2H, m; 2.9 to 2.85 ppm 3H, 2s; 2.9 to 2.6 ppm, 2H, m; 2.3 to 2.35 ppm, 2H, 2t; 1.6 to 1.85 ppm, 6H, m; 1 ppm, 3H, 2T; 2.6 ppm, 1H, s broad.

Stage C

N-{1-[(4-oxo-4H-chromen-2-yl)-methyl]-piperid-4-yl}-N-methylbutanamide was obtained in accordance with the process described in Stage D of Example 1 from (4-oxo-4H-chromen-2)-methyl iodide and the compound obtained in the above Stage.

Yield: 20%

Melting point: 127°–130° C.

Elemental analysis:

|     | Theory | Found |       |
| --- | ------ | ----- | ----- |
| C % | 70.15  | 70.31 | 69.99 |
| H % | 7.65   | 7.68  | 7.65  |
| N % | 8.18   | 7.90  | 7.96  |

EXAMPLE 3

N-{1-[4-oxo-4H-chromen-2-yl]-methyl]-piperid-4-yl}-N-methylacetamide

This compound was prepared in accordance with the process described in Example 1 but using acetyl chloride instead of propionyl chloride in Stage B.

Yield: 15%

Melting point: 118°–120° C.

Elemental analysis:

|     | Theory | Found |
| --- | ------ | ----- |
| C % | 68.17  | 68.63 |
| H % | 7.05   | 7.13  |
| N % | 8.91   | 8.73  |

EXAMPLE 4

N-{1-[(4-oxo-4H-chromen-2-yl)-methyl]-piperid-4-yl}-N-ethylpropionamide hydrochloride This compound was prepared in accordance with a process equivalent to that described in Example 1, but replacing monomethylamine by monoethylamine in Stage A.

Yield (base): 45%

Yield (salt): 80%

Melting point (salt): 230°–232° C.

Elemental analysis:

|      | Theory | Found |       |
| ---- | ------ | ----- | ----- |
| C %  | 63.40  | 63.28 | 63.11 |
| H %  | 7.18   | 7.08  | 7.05  |
| N %  | 7.39   | 7.36  | 7.35  |
| Cl % | 9.36   | 9.36  | 9.35  |

EXAMPLE 5

N-{(1-[2-(4-oxo-4H-chromen-2-yl)-ethyl]-piperid-4-yl}-N-methylpropionamide hydrochloride

Stage A

.N-{1-[2-(ethoxycarbonyl)-ethyl]-piperid-4-yl}-N-.methylpropionamide 14 g of ethyl acrylate in 45 ml of ethanol are added dropwise to 23.8 g of the amine obtained in Stage C of Example 1 dissolved in 45 ml of ethanol. The mixture is stirred at room temperature for 3 hours, evaporated, and the residual oil is distilled in a Kugelrohr (bulb tube) at 120° C. and 0.09 mg Hg.

Yield: 90%

Proton nuclear magnetic resonance spectrum (solvent CDCl$_3$): 4.5+3.6 ppm, 1H, m; 4.2 ppm, 2H, q; 3 ppm, 2H, m; 2.85 ppm, 3H, 2s; 2.7 ppm, 2H, t; 2.5 ppm, 2H, t; 2.35 ppm, 2H, 2q; 2.1 ppm, 2H, m; 1.5 to 2 ppm, 4H, m; 1.25 ppm, 3H, t; 1.15 ppm, 3H, 2t.

Stage B

N-{1-[3,5-dioxo-5-(2-hydroxyphen-1-yl)-pent-1-yl]-piperid-4-yl}-N-methylpropionamide hydrochloride A mixture comprising 34 g of the compound obtained in the above Stage, and 16.3 g of ortho-hydroxyacetophenone dissolved in 90 ml of dioxane, are poured onto 14.4 g of 60% sodium hydride in 120 ml of dioxane preheated to 80° C. The mixture is left for 1 hour at 80° C., diluted with water and acidified in the cold. The precipitate is filtered off and dried to yield the desired compound.

Yield: 22%

Melting point: >260° C.

Proton nuclear magnetic resonance spectrum (solvent $D_2O$ +NaOD): 7.15 ppm, 2H, m; 6.6 ppm, 1H, d; 6.5 ppm, 1H t; 4.3 and 3.75 ppm, 1H, 2m; 3.0 to 2.55 ppm, 9H, m; 2.55 to 2.3 ppm, 4H, m+t+q; 2.2 ppm, 2H, m; 1.95 to 1.5 ppm, 4H, m; 1.1 ppm, 3H, 2t.

Stage C 2.5 g of the compound obtained in Stage B are stirred for one night with 25 ml of 3.7N methanolic hydrogen chloride.

The mixture is filtered and the residue is dried over potassium hydroxide to yield N-{1-[2-(4-oxo-4H-chromen-2-yl)-ethyl]-piperid-4-yl}-N-methylpropionamide hydrochloride.

Yield: 65%

Melting point: 248°–250° C.

Elemental analysis:

|   | Theory | Found |
|---|---|---|
| C % | 63.40 | 63.71 |
| H % | 7.18 | 7.02 |
| N % | 7.39 | 7.33 |
| Cl % | 9.36 | 9.61 |

EXAMPLE 6

Ethyl N-[1-[(4-oxo-4H-chromen-2-yl)-methyl]-piperid-4-yl}-N-methylcarbamate hydrochloride

Stage A

Ethyl N-(1-benzylpiperid-4-yl)-N-methylcarbamate

This compound was prepared from the compound described in Stage A of Example 1 in accordance with the process described in Stage B of Example 1 but replacing propionyl chloride with ethyl chloroformate.

Yield: 89%

Proton nuclear magnetic resonance spectrum (solvent $CDCl_3$): 7.3 ppm, 5H, m; 4.1 ppm, 2H, g; 4 ppm, 1H, m; 3.5 ppm, 2H, s; 2.95 ppm, 2H, m; 2.8 ppm, 3H, s; 2.1 ppm, 2H, m; 1.9 to 1.5 ppm, 4H, m; 1.25 ppm, 3H, t.

Stage B

Ethyl N-piperid-4-yl-N-methylcarbamate 49 g of the compound obtained in Stage A dissolved in 500 ml of acetic acid in the presence of 1 g of 5% Pd/C are hydrogenated at 50° C. under 5 Kg. The catalyst is filtered off, the filtrate is evaporated, recovered with diethyl ether and rendered basic in the cold with 50 ml of sodium hydroxide solution. The ethereal phase is dried and evaporated to yield the desired compound.

Yield: 61%

Proton nuclear magnetic resonance spectrum (solvent $CDCl_3$): 4.15 ppm, 2H, q; 3.9–4.2 ppm, 1H m; 3.15 ppm, 2H, m; 2.8 ppm, 3H, s; 2.65 ppm, 2H, m; 1.6 ppm, 4H, m; 1.25 ppm, 3H, 1H exchangeable.

Stage C

Ethyl N-(1-[(4-oxo-4H-chromen-2-yl)-methyl]-piperid-4-yl}-N-methylcarbamate is obtained from the compound described in Stage B and in accordance with the process described in Stage D of Example 1.

Yield: 65%

4.3 g of these base are dissolved in 20 ml of acetonitrile and 3.5 ml of 3.8N ethereal hydrogen chloride are added to obtain ethyl N-{1-[(4-oxo-4H-chromen- 2-yl)-methyl]-piperid-4-yl)-N-methylcarbamate hydrochloride.

Yield: 73%

Melting point: >260° C.

Elemental analysis:

|   | Theory | Found |   |
|---|---|---|---|
| C % | 59.92 | 59.73 | 59.52 |
| H % | 6.62 | 6.58 | 6.59 |
| N % | 7.36 | 7.06 | 7.10 |
| Cl % | 9.31 | 9.30 | 9.09 |

EXAMPLE 7

N-{1-[(4-oxo-4H-chromen-2-yl)-methyl]-piperid-4-yl}-N-methylisobutylamide hydrochloride This compound was obtained in accordance with the process described in Example 1 but replacing propionyl chloride with isobutyl chloride in Stage B.

Yield (base): 65%

Yield (salt): 67%

Melting point (salt): 248°–250° C.

Elemental analysis:

|   | Theory | Found |   |
|---|---|---|---|
| C % | 63.40 | 63.28 | 63.34 |
| H % | 7.18 | 7.22 | 7.28 |
| N % | 7.39 | 7.40 | 7.44 |
| Cl % | 9.36 | 9.48 | 9.30 |

EXAMPLE 8

Methyl [1-(benzocyclobuten-1-ylmethyl)-piperid-4-yl]-N-methylcarbamate hydrochloride

Stage A

Methyl N-(1-benzylpiperid-4-yl)-N-methylcarbamate

This compound was prepared in accordance with the process described in Stage B of Example 1 using methyl chloroformate instead of propionyl chloride.

Yield: 7%

Proton nuclear magnetic resonance spectrum (solvent $CDCl_3$): 7.3 ppm, 5H, m; 3.7 to 4.1 ppm, 1H m; 3.7 ppm, 3H, s; 3.5 ppm, 2H, s; 2.95 ppm, 2H, d; 2.75 ppm, 3H, s; 2.1 ppm, 2H, t; 1.5 to 1.9 ppm, 4H, m.

Stage B

Methyl N-piperid-4-yl-N-methylcarbamate

The carbamate described in the above Stage is subjected to hydrogenation under 5 Kg at 50° C. in ethanol in the presence of 5% Pd/C and a suitable amount of concentrated hydrochloric acid to yield the corresponding hydrochloride. Conversion to the base in the presence of diethyl ether and 40% sodium hydroxide solution yields the desired compound.

Yield: 53%

Proton nuclear magnetic resonance spectrum (solvent CDCl$_3$): 4.1 ppm, 1H, m; 3.7 ppm, 3H, m; 3.15 ppm, 2H, m; 2.8 ppm, 3H, d; 2.6 to 2.9 ppm, 2H, m; 1.5 to 1.7 ppm, 4H, m; 1.75 ppm, 1H exchangeable.

Stage C 7.3 g of 1-iodomethylbenzocyclobutene (prepared in accordance with the process described in Patent Application FR 89.14571 of Nov. 7, 1989) and 5.1 g of the compound obtained in Stage B in 100 ml of dimethylformamide are heated at 60° C. for 6 hours with stirring.

The solvent is evaporated, the residue is taken up in water, extracted with diethyl ether and then the ethereal phase is extracted with N hydrochloric acid. The extract is rendered basic in the cold and extracted with diethyl ether to yield methyl N-[1-(benzocyclobuten-1-ylmethyl)-piperid-4-yl]-N-methylcarbamate.

Yield: 43%

3.7 g of this base dissolved in 30 ml of ethanol are converted into a salt with 10 ml of 3N ethereal hydrogen chloride to yield the corresponding hydrochloride.

Yield: 59%

Melting point: >260° C.

Elemental analysis:

|     | Theory | Found |       |
| --- | ------ | ----- | ----- |
| C % | 62.86  | 62.85 | 62.51 |
| H % | 7.76   | 7.95  | 7.70  |
| N % | 8.62   | 8.57  | 8.43  |
| Cl %| 10.91  | 10.97 | 10.54 |

EXAMPLE 9

Propyl N-[1-(benzocyclobuten-1-ylmethyl)-piperid-4-yl]-N-methylcarbamate hydrochloride This compound was obtained in accordance with the process described in Example 8 but using propyl chloroformate instead of methyl chloroformate in Stage A.

Yield (base): 28%
Yield (salt): 73%
Melting point: 248°-250° C.
Elemental analysis:

|     | Theory | Found |       |
| --- | ------ | ----- | ----- |
| C % | 64.67  | 64.35 | 64.18 |
| H % | 8.28   | 8.48  | 8.40  |
| N % | 7.94   | 7.95  | 7.93  |
| Cl %| 10.05  | 10.17 | 10.05 |

EXAMPLE 10

N-[1-(benzocyclobuten-1-ylmethyl)-piperid-4-yl]-N-methylpentafluoropropionamide hydrochloride This compound was prepared in accordance with the process described in Example 8 but using pentafluoropropionyl chloride instead of methyl chloroformate in Stage A.

Yield (salt): 10.5%
Melting point: 246°-248° C.
Elemental analysis:

|     | Theory | Found |       |
| --- | ------ | ----- | ----- |
| C % | 52.37  | 52.56 | 52.56 |
| H % | 5.37   | 5.54  | 5.53  |
| N % | 6.79   | 6.78  | 6.68  |
| Cl %| 8.59   | 8.85  | 8.49  |

EXAMPLE 11

Tert-butyl N-[1-(benzocyclobuten-1-ylmethyl)-piperid-4-yl]-N-methylcarbamate hydrochloride

Stage A

Tert-butyl N-(1-benzylpiperid-4-yl)-N-methylcarbamate 24 g of tert-butyl pyrocarbonate are poured onto 27.8 g of the amine obtained in Stage A of Example 1 in 200 ml of dioxane and 200 ml of 1N sodium hydroxide solution while maintaining the temperature at 5° C. The mixture is left for one hour at 5° C. and then extracted with diethyl ether.

The residual oil is subjected to flash chromatography using a mixture of methylene chloride and ethyl acetate (80:20 v/v) as solvent to yield the desired compound.

Yield: 66%

Proton nuclear magnetic resonance spectrum (solvent CDCl$_3$): 7.3 ppm, 5H, m; 4.2 to 3.7 ppm, 1H, s; 3.5 ppm, 2H, s; 2.95 ppm, 2H, m; 2.75 ppm, 3H, s; 2.05 ppm, 2H, m; 1.9 to 1.55 ppm, 4H, m; 1.45 ppm, 9H, s.

Stage B

Tert-butyl N-piperid-4-yl-N-methylcarbamate 20 g of the compound obtained in the above Stage, in 200 ml of ethanol and 3.6 g of acetic acid are subjected to hydrogenation with 2 g of 5% Pd/C under 5Kg at 5° C.

After evaporation, removal of the acetate with sodium hydroxide solution in the presence of diethyl ether and decanting, the residue is dried and evaporated to yield the desired compound.

Yield: 71%
Melting point: <50° C.

Proton nuclear magnetic resonance spectrum (solvent CDCl$_3$): 4 ppm, 1H, m; 3.1 ppm, 2H, m; 2.7 ppm, 3H, s; 2.6 ppm, 2H, m; 1.4 to 1.7 ppm, 4H, m; 1.45 ppm, 9H, s; 1.65 ppm, 1H exchangeable.

Stage C

Tert-butyl N-[1-(benzocyclobuten-1-ylmethyl)-piperid-4-yl]-N-methylcarbamate hydrochloride is obtained in accordance with the process described in Stage C of Example 8 from 1-iodomethylbenzocyclobutene and tert-butyl N-piperid-4-yl-N-methylcarbamate.

Yield: 60%

Melting point: >260° C.
Elemental analysis:

|   | Theory | Found |
|---|---|---|
| C % | 65.47 | 64.97 |
| H % | 8.52  | 8.63  |
| N % | 7.63  | 7.53  |
| Cl % | 9.66 | 9.84  |

EXAMPLE 12

Phenyl N-[1-(benzocyclobuten-1-ylmethyl)-piperid-4-yl]-N-methylcarbamate hydrochloride This compound was prepared in accordance with the process described in Example 8 but using phenyl chloroformate instead of propionyl chloride in Stage A.
Yield: 21%
Melting point: 262°-264° C.
Elemental analysis:

|   | Theory | Found | |
|---|---|---|---|
| C % | 68.29 | 67.71 | 67.76 |
| H % | 7.03  | 7.52  | 7.08  |
| N % | 7.24  | 7.01  | 6.98  |
| Cl % | 9.16 | 9.16  | 9.09  |

EXAMPLE 13

Ethyl N-[1-(benzocyclobuten-1-ylmethyl)-piperid-4-yl]-N-ethylcarbamate hydrochloride This compound was prepared in accordance with the process described in Example 8 but from 1-benzyl-4-ethylaminopiperidine dihydrochloride and replacing the methyl chloroformate with ethyl chloroformate in Stage A.
Yield: 13%
Melting point: 258°-260° C.
Elemental analysis:

|   | Theory | Found | |
|---|---|---|---|
| C % | 64.67 | 64.42 | 64.51 |
| H % | 8.28  | 8.69  | 8.69  |
| N % | 7.94  | 7.83  | 7.75  |
| Cl % | 10.05 | 10.25 | 9.96  |

EXAMPLE 14

Methyl N-[1-(benzocyclobuten-1-ylmethyl)-piperid-4-yl]-N-ethylcarbamate hydrochloride This compound was prepared in accordance with the process described in Example 8 using 1-benzyl-4-ethylaminopiperidine and methyl chloroformate in Stage A.
Yield: 13%
Melting point: 258°-260° C.
Elemental analysis;

|   | Theory | Found | |
|---|---|---|---|
| C % | 63.80 | 63.92 | 63.71 |
| H % | 8.03  | 8.34  | 8.18  |
| N % | 8.27  | 8.07  | 8.10  |
| Cl % | 10.46 | 10.57 | 10.39 |

EXAMPLE 15

Isobutyl N-[1-(benzocyclobuten-1-ylmethyl)-piperid-4-yl]-N-methylcarbamate fumarate The base was prepared also in accordance with the process described in Example 8 using isobutyl chloroformate instead of methyl chloroformate in Stage A.

The isobutyl N-[1-(benzocyclobuten-1-ylmethyl)-piperid-4-yl]-N-methylcarbamate so obtained is then converted into a salt with an appropriate amount of fumaric acid in ethanol.
Yield: 27%
Melting point: 190°-192° C.
Elemental analysis:

|   | Theory | Found | |
|---|---|---|---|
| C % | 64.55 | 64.60 | 64.50 |
| H % | 7.67  | 7.94  | 7.82  |
| N % | 6.29  | 6.31  | 6.35  |

EXAMPLE 16

N-[1-(benzocyclobuten-1-ylmethyl)-piperid-4-yl]-propionamide hydrochloride

Stage A 1-benzyl-4-hydroxyiminopiperidine 18.9 g of 1-benzyl-4-oxopiperidine, 26.8 g of hydroxylamide hydrochloride, and 24.8 g of sodium acetate in 200 ml of ethanol are stirred for 8 hours.

The mixture is concentrated, taken up in 100 ml of water and rendered basic and the resulting precipitate is filtered off.
Yield: 98%
Melting point: 125°-127° C.
Proton nuclear magnetic resonance spectrum (solvent CDCl$_3$): 7.3 ppm, 5H, m; 3.55 ppm, 2H, s; 2.75 to 2.4 ppm, 6H, m; 2.35 ppm, 2H, m; 3 ppm, 1H exchangeable.

Stage B 4-amino-1-benzylpiperidine 9.3 g of the oxime obtained in the above Stage are hydrogenated in 230 ml of ethanol and 9.3 ml of ammonia in the presence of Raney nickel at atmospheric pressure and at room temperature.

The desired compound is obtained after filtering off the catalyst and evaporating the solvent.
Yield: 80%
Proton nuclear magnetic resonance spectrum (solvent CDCl$_3$); 7.3 ppm, 5H, m; 3.4 ppm, 2H, s; 2.8 ppm, 2H, m; 2.6 ppm, 1H, m; 2 ppm, 2H, m; 1.8 ppm, 2H, m; 1.4 ppm, 2H, m; 1.4 ppm, 2H exchangeable.

Stage C

N-(1-benzylpiperid-4-yl)-propionamide 7.5 g of propionyl chloride are added dropwise to 10 g of amine described in Stage B in 100 ml of benzene and 7.7 ml of triethylamine.

The mixture is decanted to a separating funnel, diluted with diethyl ether, washed with water, dried and evaporated.

Yield: 83%

Melting point: 105°–107° C.

Proton nuclear magnetic resonance spectrum (solvent CDCl$_3$): 7.25 ppm, 5H, m; 4.8 and 3.7 ppm, 1H, 2m; 3.5 ppm, 2H, s; 2.8 ppm, 2H, m; 2.1 ppm, 2H, q; 2.1 ppm, 2H, m; 1.9 ppm, 2H, m; 1.45 ppm, 2H, m; 1.15 ppm, 3H, t; 5.35 ppm, 1H exchangeable.

Stage D

N-piperid-4-ylpropionamide acetate

The debenzylation of the amide obtained in Stage C is carried out in accordance with the method described in Stage B of Example 11 to yield the desired acetate after evaporation and solidification with diethyl ether.

Yield: 48%

Melting point: 128°–130° C.

Proton nuclear magnetic resonance spectrum (solvent CDCl$_3$): 8.35 ppm, 2H exchangeable; 6.65 ppm, 1H exchangeable; 3.95 ppm, 1H, m; 3.3 ppm, 2H, m; 2.35 ppm, 2H, td; 2.2 ppm, 2H, q; 1.95 ppm, 3H, s; 2.1 to 1.6 ppm, 4H, m; 1.1 ppm, 3H, t.

Stage E

N-[1-(benzocyclobutene-1-ylmethyl)-piperid-4-yl]-propionamide hydrochloride was prepared in accordance with the process described in Stage C of Example 8 from N-piperidin-4-ylpropionamide acetate and 1-iodomethylbenzocyclobutene.

Yield: 17%

Melting point: 262°–264° C.

Elemental analysis:

|     | Theory | Found |
| --- | --- | --- |
| C % | 66.11 | 65.87 |
| H % | 8.16 | 8.35 |
| N % | 9.07 | 9.03 |
| Cl % | 11.48 | 11.57 |

EXAMPLE 17

2-methoxyethyl N-[1-(benzocyclobuten-1-ylmethyl)-piperid-4-yl]-N-methylcarbamate hydrochloride This compound was prepared in accordance with the process described in Example 11 (Stages B and C) but using 2-methoxyethyl N-(1-benzylpiperid-4-yl)-N-methylcarbamate in Stage B. The latter is obtained in accordance with the process described in Stage B of Example 1 using methoxyethyl chloroformate instead of propionyl chloride.

Yield: 14%

Melting point: 210°–212° C.

Elemental analysis:

|     | Theory | Found | |
| --- | --- | --- | --- |
| C % | 61.86 | 61.81 | 61.69 |
| H % | 7.92 | 7.92 | 8.03 |
| N % | 7.59 | 7.51 | 7.23 |
| Cl % | 9.61 | 9.78 | 9.53 |

EXAMPLE 18

Cyclohexyl N-[(benzocyclobuten-1-ylmethyl)-piperid-4-yl]-N-methylcarbamate hydrochloride This compound was prepared in accordance with the process described in Stages B and C of Examples 11, but using cyclohexyl N-(1-benzylpiperid-4-yl)-N-methylcarbamate in Stage B. The latter is obtained in accordance with the process described in Stage B of Example 1 using hexyl chloroformate.

Yield: 13%

Melting point: 262°–264° C.

Elemental analysis:

|     | Theory | Found | |
| --- | --- | --- | --- |
| C % | 67.24 | 66.77 | 66.72 |
| H % | 8.46 | 8.53 | 8.64 |
| N % | 7.13 | 7.35 | 7.33 |
| Cl % | 9.02 | 8.48 | 8.57 |

EXAMPLE 19

Benzyl N-[1-(benzocyclobuten-1-ylmethyl)-piperid-4-yl]-N-methylcarbamate hydrochloride

Stage A 1-acetyl-4-methylaminopiperidine 9.9 g of methylamine in 50 ml of ethanol are added to 14.4 g of 1-acetyl-4-oxopiperidine in 100 ml of ethanol. The mixture is then hydrogenated in the presence of platinum oxide at room temperature and atmospheric pressure, filtered and evaporated.

Yield: 98%

Proton nuclear magnetic resonance spectrum (solvent CDCl$_3$): 4.4 to 3.7 ppm, 2H, m; 3.1 to 2.7 ppm, 2H, s; 2.6 ppm, 1H, m; 2.45 ppm, 3H, s; 2.05 ppm, 3H, s; 1.35 and 1.2 ppm, 4H, m; 1.7 ppm, 1H exchangeable.

Stage B

Benzyl N-(1-acetylpiperid-4-yl)-N-methylcarbamate

The amine obtained in Stage A is treated with benzyl chloroformate in accordance with the process described in Stage B of Example 1 to obtain the desired carbamate.

Yield: 54%

Proton nuclear magnetic resonance spectrum (solvent CDCl$_3$): 7.35 ppm, 5H, m; 5.1 ppm, 2H, s; 4.75 ppm, 1H, m; 4.2 ppm, 1H, m; 3.85 ppm, 1H, m; 3.1 ppm, 1H, t; 2.8 ppm, 3H, s; 2.55 ppm, 1H, t; 2.1 ppm, 3H, s; 1.8 to 1.4 ppm, 4H, m.

Stage C

Benzyl N-piperid-4-yl-N-methylcarbamate hydrochloride 14.5 g of the compound obtained in Stage B are refluxed with 50 ml of methanol and 30 ml of 6N hydrochloride acid for 20 hours. After evaporation the hydrochloride of the desired product is obtained.

Yield: 83%

Melting point: 203°–205° C.

Proton nuclear magnetic resonance spectrum (solvent CDCl$_3$): 7.4 ppm, 5H, m; 5.15 ppm, 2H, s; 4.3 ppm, 2H, m; 3.6 ppm, 2H, d; 2.95 ppm, 2H, m; 2.85 ppm, 3H, s; 2.25 ppm, 2H, m; 1.85 ppm, 2H, d.

Stage D

Benzyl N-[1-(benzocyclobuten-1-ylmethyl)-piperid-4-yl]-N-ethylcarbamate hydrochloride was prepared from benzyl N-piperid-4-yl-N-methylcarbamate hydrochloride and 1-iodomethylbenzocyclobutene, in accordance with the process described in Stage C of Example 8, in the presence of triethylamine.

Yield: 22.5%
Melting point: 210°–212° C.
Elemental analysis:

|  | Theory | Found | |
|---|---|---|---|
| C % | 68.90 | 68.84 | 68.97 |
| H % | 7.29 | 7.43 | 7.55 |
| N % | 6.99 | 7.06 | 7.08 |
| Cl % | 8.84 | 9.00 | 8.79 |

EXAMPLE 20

N-{1-[(1-methylbenzocyclobuten-1-yl)-methyl]-piperid-4-yl}-N-methylpropionamide hydrochloride This compound was obtained from 1-methyl-1-iodomethylbenzocyclobutene (prepared in accordance with the process described in the Patent Application FR 89.14571 of Nov. 7, 1989) and N-piperid-4-yl-N-methylpropionamide in accordance with the process described in Stage C of Example 8.

Yield: 14.5%
Melting point: 222° C.
Elemental analysis:

|  | Theory | Found |
|---|---|---|
| C % | 67.74 | 67.43 |
| H % | 8.68 | 8.59 |
| N % | 8.31 | 8.24 |
| Cl % | 10.52 | 10.65 |

EXAMPLE 21

N-[1-(benzocyclobuten-1-ylmethyl)-piperid-4-yl]-N-ethylacetamide hydrochloride 3.3 g of N-piperid-4-yl-N-ethylacetamide and 2.8 g of 1-methylbenzocyclobutene tosylate (prepared in accordance with the process described in J.A.C.S., (1975), 154, p. 347) are refluxed under nitrogen for 20 hours in 16 ml of toluene. After cooling, the reaction mixture is evaporated to dryness and taken up in diethyl ether. After extraction with N hydrochloric acid, the extract is rendered basic in the presence of diethyl ether and the organic phase is washed with water, dried over magnesium sulphate and evaporated in vacuo to yield N-[1-(benzocyclobuten-1-ylmethyl)-piperid-4-yl]-N-ethylacetamide. The corresponding hydrochloride is obtained in ethyl acetate in the presence of ethereal hydrogen chloride.

Yield: 20.7%
Melting point: 265°–267° C.
Elemental analysis:

|  | Theory | Found |
|---|---|---|
| C % | 66.96 | 67.08 |
| H % | 8.43 | 8.55 |
| N % | 8.68 | 8.59 |
| Cl % | 10.98 | 11.02 |

EXAMPLE 22

N-[1-(benzocyclobuten-1-ylmethyl)-piperid-4-yl)-N-methylpropionamide hydrochloride This compound was prepared in accordance with the process described in Example 21 using N-piperid-4-yl-N-methylpropionamide as amide.

Yield: 28%
Melting point: 203°–306° C.
Elemental analysis:

|  | Theory | Found | |
|---|---|---|---|
| C % | 66.96 | 66.67 | 67.00 |
| H % | 8.43 | 8.24 | 8.10 |
| N % | 8.68 | 8.62 | 8.66 |
| Cl % | 10.98 | 10.87 | 10.87 |

EXAMPLE 23

Ethyl N-[1-(benzocyclobuten-1-ylmethyl)-piperid-4-yl]-N-methylcarbamate hydrochloride This compound was prepared in accordance with the process described in Example 21 using ethyl N-piperid-4-yl-N-methylcarbamate instead of N-piperid-4-yl-N-ethylacetamide.

Yield: 58%
Melting point: 305°–313° C.
Elemental analysis:

|  | Theory | Found | |
|---|---|---|---|
| C % | 63.80 | 63.55 | 63.84 |
| H % | 8.03 | 7.80 | 8.00 |
| N % | 8.27 | 8.44 | 8.49 |
| Cl % | 10.46 | 10.78 | 10.78 |

EXAMPLE 24

N-[1-(benzocyclobuten-1-ylmethyl)-piperid-4-yl]-N-methylbutyramide hydrochloride 4 g of the compound obtained in Stage B of Example 2 and 3.1 g of 1-methylbenzocyclobutene tosylate are refluxed under nitrogen for 18 hours in 20 ml of toluene. After cooling, the reaction mixture is evaporated to dryness and taken up in diethyl ether.

After extraction with N hydrochloric acid, the extract is rendered basic in the presence of diethyl ether, and the organic phase is washed with water and dried over magnesium sulphate. After evaporation of the solvent in vacuo, the base obtained is taken up in ethyl acetate and treated with ethereal hydrogen chloride to obtain the desired compound.

Yield: 47%
Melting point: 238° C.
Elemental analysis:

|  | Theory | Found | |
|---|---|---|---|
| C % | 67.74 | 67.48 | 67.55 |
| H % | 8.68 | 8.83 | 8.86 |

| | Theory | Found | |
|---|---|---|---|
| N % | 8.31 | 8.24 | 8.28 |
| Cl % | 10.52 | 10.59 | 10.45 |

EXAMPLE 25

Allyl N-[1-(benzocyclobuten-1-ylmethyl)-piperid-4-yl]-N-methylcarbamate hydrochloride

Stage A

N-(1-acetylpiperid-4-yl)-N-benzylmethylamine

A mixture containing 0.5 mol of the compound obtained in Stage A of Example 19, 0.5 M benzyl chloride and 1 M sodium carbonate in 650 ml of ethanol is refluxed for one night. The precipitate formed is filtered off, the solvent is evaporated, the evaporation residue is taken up in 1N hydrochloric acid and extracted with diethyl ether, and the ethereal extract is rendered basic with sodium hydroxide solution and extracted with ethyl acetate to obtain the desired compound.

Yield: 65%

Proton nuclear magnetic resonance spectrum (solvent $CDCl_3$): 7.25 ppm, 5H, m; 4.6 ppm, 1H, m; 3.8 ppm, 1H, m; 3.55 ppm, 2H, s; 3 ppm, 1H, td; 2.7 to 2.4 ppm, 2H, m; 2.2 ppm, 3H, s; 2.05 ppm, 3H, s; 1.85 ppm, 2H, m; 1.55 ppm, 2H, m.

Stage B 4-(N-benzyl-N-methylamino)-piperidine 80 g of the compound obtained in the above Stage dissolved in 375 ml of methanol are treated with 97.5 ml of concentrated hydrochloric acid and 97.5 ml of water for 2 hours under reflux. The reaction solution is evaporated and rendered basic and extracted with diethyl ether to obtain the desired compound.

Yield: 85.5%

Stage C 1-(benzocyclobuten-1-ylcarbonyl)-4-(N-benzyl-N-methylamino)-piperidine 41 g of carbonyldiimidazole are added to a solution of 36.2 g of benzocyclobuten-1-ylcarboxylic acid in 400 ml of methylene chloride. The mixture is stirred for 4 hours and the compound obtained in the above Stage, dissolved in methylene chloride, is added. The reaction mixture is refluxed for 72 hours, diluted with 1500 ml of diethyl ether and extracted 3 times with 100 ml of 0.1N hydrochloric acid. The aqueous phases are removed and the organic phase is re-extracted three times with 100 ml of 1N hydrochloric acid. The acidic aqueous phases are then rendered basic and extracted with diethyl ether to obtain the desired compound.

Yield: 34%

Proton nuclear magnetic resonance spectrum (solvent $CDCl_3$): 7.4 to 7 ppm, 9H, m; 4.65 ppm, 1H, m; 4.45 ppm, 1H, m; 4.15 ppm, 1H, m; 3.6 ppm, 2H, s; 3.6 to 3.3 ppm, 2H, m; 3.15 ppm, 1H, m; 2.8 to 2.5 ppm, 1H+1H, m; 2.25 ppm, 3H, s; 2 ppm, 2H, m; 1.8 to 1.4 ppm, 2H, m.

Stage D

1-{[4-(N-benzyl-N-methylamino)-piperid-1-yl]-methyl)-benzocyclobutene 28 g of the compound obtained in Stage C dissolved in 150 ml of tetrahydrofuran are poured onto a suspension of 3.2 g of lithium aluminium hydride in 50 ml of tetrahydrofuran. The reaction mixture is refluxed for 3 hours, treated in customary manner, filtered, and the organic phase is evaporated to isolate the desired compound.

Yield: 84.5%

Proton nuclear magnetic resonance spectrum (solvent $CDCl_3$): 7.3 to 6.9 ppm, 9H, m; 3.7 ppm, 1H, m; 3.55 ppm, 2H, s; 3.35 ppm, 1H, dd; 3.1 ppm, 2H, 2.8 ppm, 1H+1H, m; 2.6 to 2.4 ppm, 2H, m; 2.2 ppm, 3H, s; 2.05 ppm, 2H, m; 1.9 to 1.6 ppm, 4H, m.

Stage E

1-[(4-methylaminopiperid-1-yl)-methyl]-benzocyclobutene 22 g of the compound obtained in Stage D in 220 ml of ethanol and 4.2 ml of acetic acid containing 2.2 g of 5% Pd/C are hydrogenated at 50° C. under 5 atmospheres. The catalyst is removed by filtration, the filtrate is evaporated and then coagulated by stirring with 20 ml of diethyl ether and then the product is rendered alkaline with 20% sodium hydroxide in the presence of 200 ml of diethyl ether, in order to precipitate the desired product.

Yield: 77%

Proton nuclear magnetic resonance spectrum (solvent $CDCl_3$): 7.4–7 ppm, 4H, m; 3.75–3.6 ppm, 1H, m; 3.45 to 3.25 ppm, 1H, m; 3.05 to 2.9 ppm, 2H, m; 3 to 2.5 ppm 1H+1H, m; 2.45 ppm, 3H, s; 2.2 to 2 ppm, 2H, m; 2.0 to 1.8 ppm, 2H, m; 1.55 to 1.3 ppm, 2H, m; 2 to 1.7 ppm, 1H exchangeable; 2.8 ppm, 1H, m; 2.5 to 2.3 ppm, 1H, m.

Stage F 1.4 ml of allyl chloroformate dissolved in 5 ml of benzene are poured onto 1.8 ml of triethylamine 3 g of the compound obtained in the above Stage dissolved in 30 ml of benzene. The mixture is diluted with diethyl ether, washed with water, dried and evaporated. The residue obtained is diluted in 10 ml of ethyl acetate and 3.3 ml of 3.6N ethereal hydrogen chloride are added to yield allyl N-[1-(benzocyclobuten-1-ylmethyl)-piperid-4-yl]-N-methylcarbamate hydrochloride.

Yield: 53%

Melting point: 233°–235° C.

Elemental analysis:

| | Theory | Found | |
|---|---|---|---|
| C % | 65.04 | 64.84 | 64.90 |
| H % | 7.76 | 7.66 | 7.87 |
| N % | 7.98 | 7.98 | 7.86 |
| Cl % | 10.10 | 10.05 | 9.88 |

EXAMPLE 26

N-[1-(benzyocyclobuten-1-ylmethyl)-piperid-4-yl]-N-methylacrylamide hydrochloride This compound was obtained in accordance with the process described in Stage F of Example 25 but replacing allyl chloroformate with acryloyl chloride.

Yield: 24%
Melting point: 230°-232° C.
Elemental analysis:

|  | Theory | Found |
|---|---|---|
| C % | 67.38 | 67.04 |
| H % | 7.85 | 7.80 |
| N % | 8.73 | 8.66 |
| Cl % | 11.05 | 11.14 |

EXAMPLE 27

N-{(1-[(1,2-dihydro-1-(2-fluorophenyl)-2-oxo-1,8-naphthyridin-3-yl)-methyl]-piperid-4-yl)-N-methylpropionamide

Stage A

2-[(2-fluorophenyl)-amino]-nicotinic acid 50 g of 2-chloronicotinic acid and 31 ml of 2-fluoroaniline in 180 ml of xylene are refluxed for 5 hours. The precipitate is filtered off and washed with xylene and then with water to yield the desired compound.
Melting point: 114° C.
Proton nuclear magnetic resonance spectrum (solvent DMSO-$d_6$): 10.65 ppm, 1H exchangeable; 8.1 to 8.6 ppm, 3H m+1H exchangeable; 6.8 to 7.4 ppm, 5H, m.

Stage B 2-(2-fluorophenyl)-amino-3-hydroxymethylpyridine 59.3 g of the compound obtained in the above Stage are dissolved hot in tetrahydrofuran and the solution is poured onto 19.5 g of lithium aluminum hydride suspended in tetrahydrofuran. After hydrolysis, the mixture is filtered, then concentrated and purified on a silica column, using methylene chloride as eluant, to yield the desired compound.
Yield: 25%
Melting point: 96%

Stage C

2-[(2-fluorophenyl)-amino]-3-formylpyridine 13.5 g of the compound obtained in Stage B are dissolved in 200 ml of methylene chloride and then 65 g of manganous oxide are added. The mixture is stirred at room temperature for 48 hours. A further 10 g of manganous oxide is added and the mixture is left for 24 hours and then filtered, the residue is washed several times with methylene chloride, and the filtrate and washings are concentrated and purified on a silica column to yield the desired compound.
Yield: 43%
Melting point: 94° C.
Proton nuclear magnetic resonance spectrum (solvent CDCl$_3$): 10.6 ppm, 1H exchangeable; 9.95 ppm, 1H, s; 8.85 ppm, 1H, t; 8.45 ppm, 1H, d; 7.9 ppm, 1H, d; 7.2 to 7.0 ppm, 3H, m; 6.9 ppm, 1H, dd.

Stage D

N-[1-(ethoxycarbonylethyl)-piperid-4-yl]-N-methylpropionamide 7.4 g of the compound obtained in Stage C of Example 1 are dissolved in 10 ml of ethanol, then 4.73 ml of ethyl acrylate dissolved in 12 ml of ethanol are poured onto the solution. The mixture is left at room temperature for one night, and then concentrated in a rotary evaporator and distilled in a Kugelrohr to yield the compound in the form of an oil.
Yield: 88%
Proton nuclear magnetic resonance spectrum (solvent CDCl$_3$): 4.5 and 3.6 ppm, 1H, 2m; 4.2 ppm, 2H, g; 3 ppm, 2H, m; 2.85 ppm, 3H, 2s; 2.7 ppm, 2H, t; 2.5 ppm, 2H, t; 2.35 ppm, 2H, 2q; 2.1 ppm, 2H, m; 2 to 1.5 ppm, 4H, m; 1.25 ppm, 3H, t; 1.15 ppm, 3H, 2t.

Stage E 2.2 g of the compound obtained in Stage C and 2.8 g of the compound obtained in stage D dissolved in 15 ml of benzene are poured onto 0.4 g of sodium hydride covered with 15 ml of benzene and the reaction is primed with a few drops of ethanol. The reaction mixture is stirred at room temperature for 2 days and hydrolysed with 50 ml of water. The precipitate is filtered off and recrystallised from 16 ml of ethanol to yield N-[1,2-dihydro-1-(2-fluorophenyl)-2-oxo-1,8-naphthyridin-3-ylmethyl]-piperid-4-yl)-N-methylpropionamide.
Yield: 16%
Melting point: 218°-220° c.
Elemental analysis:

|  | Theory | Found | |
|---|---|---|---|
| C % | 68.23 | 68.55 | 68.27 |
| H % | 6.44 | 6.58 | 6.57 |
| N % | 13.26 | 13.24 | 13.18 |

EXAMPLE 28

Ethyl N-{1-[(3,4-methylenedioxybenzocyclobuten-1-yl)-methyl]-piperid-4-yl}-N-methylcarbamate fumarate

Stage A 2-cyano-3-(2,3-methylenedioxyphenyl)-propen-2-oic acid 160 g of 2,3-methylenedioxybenzaldehyde, 90.52 g of cyanoacetic acid, 149.2 ml of pyridine and 13.6 g of ammonium acetate are mixed together and refluxed for 12 hours in 944 ml of toluene.

Using a Dean-Stark apparatus, 17 ml of water are removed and then the mixture is left at room temperature for one night. The precipitate is filtered off, taken up in 600 ml of 18% hydrochloric acid, the mixture is filtered and the filtrate is washed with water until neutral.

The organic phase is extracted with a saturated sodium hydrogen carbonate solution. The resulting precipitate is kept and the aqueous phase is acidified and extracted with methylene chloride. The organic phase is extracted with a saturated sodium hydrogen carbonate solution. The resulting precipitate is kept and is the desired acid.
Yield: 47.5%
Melting point: 230° C.
Proton nuclear magnetic resonance spectrum (solvent DMSO-$d_6$): 8.2 ppm, 1H, s; 7.7 ppm, 1H, d; 7.15 ppm, 1H, d; 7.0 ppm, 1H, t; 6.2 ppm, 2H, s; 3.5 ppm, 1H exchangeable.

Stage B 2-cyano-3-(2,3-methylenedioxyphenyl)propanoic acid 60.2 g of sodium borohydride are added to a mixture containing 110 g of the acid obtained in Stage A and 404.5 ml of a saturated sodium hydrogen carbonate solution at 18° C. The mixture is left for 48 hours, taken up in water, washed with diethyl ether and then acidified to pH 2 with hydrochloric acid. The mixture is extracted with methylene chloride, then the organic phase is washed with water until neutral and dried to obtain the desired compound.

Yield: 55%

Melting point: 118° C.

Proton nuclear magnetic resonance spectrum (solvent $CDCl_3+DMSO-d_6$): 8.8 ppm, 1H exchangeable; 6.8 ppm, 3H, m; 6.0 ppm, 2H, m; 3.85 ppm, 1H, dd; 3.3 ppm, 1H, dd; 3.10 ppm, 1H, dd.

Stage C 2-cyano-1-(2,3-methylenedioxyphenyl)-ethane 60.6 g of acid prepared in Stage B are mixed with 115 ml of N,N-dimethylacetamide and the mixture is heated at 150° C. for approximately 2 hours and then allowed to cool, taken up in water and extracted with diethyl ether. The ethereal phases are washed with a sodium hydrogen carbonate solution and then with water and dried to yield the desired compound in the form of an oil.

Yield: 87%

Proton nuclear magnetic resonance spectrum (solvent $CDCl_3$): 6.9 to 6.65 ppm, 3H, m; 5.95 ppm, 2H, s; 2.95 ppm, 2H, t; 2.65 ppm, 2H, t.

Stage D 1-(6-bromo-2,3-methylenedioxyphenyl)-2-cyanoethane 16.4 ml of bromine dissolved in 35 ml of acetic acid are poured at 18° C. onto 53.6 g of nitrile obtained in Stage C dissolved in 179 ml of acetic acid. The mixture is stirred for 1 hour, then left overnight at room temperature and hydrolysed with 31.5 g of potassium acetate dissolved in 150 ml of water and 196.5 g of ice. The mixture is extracted with diethyl ether and the ethereal phase is washed several times with water and dried.

Yield: 24%

Melting point: 60°–65° C.

Proton nuclear magnetic resonance spectrum (solvent $CDCl_3$): 7.0 ppm, 1H, d; 6.65 ppm, 1H, d; 6.0 ppm, 2H, s; 3.05 ppm, 2H, t; 2.65 ppm, 2H, t.

Stage E 1-cyano-3,4-methylenedioxybenzocyclobutene 15 g of the compound obtained in the above Stage are added to 0.1 mol of sodium amide in liquid ammonia. The mixture is left for 15 minutes and then neutralised with 10.2 g of ammonium chloride. The ammonia is allowed to evaporate and then the residue is taken up in water and diethyl ether. The insoluble material is filtered off, the filtrate is decanted and the aqueous phase is reextracted with diethyl ether. The organic phases are combined, washed with N hydrochloric acid and then dried over magnesium sulphate.

Yield: 57%

Melting point: 80° C.

Proton nuclear magnetic resonance spectrum (solvent $CDCl_3$): 6.6 to 6.9 ppm, 2H, d; 5.95 ppm, 2H, s; 4.2 ppm, 1H, m; 3.55 ppm, 2H, m.

Stage F 3,4-methylenedioxybenzocyclobuten-1-ylcarboxylic acid 5.8 g of the compound prepared above are stirred at room temperature for one night in an ethanolic solution of potassium hydroxide (6.7 g in 48 ml of ethanol). 9 ml of water are then added and the mixture is refluxed for 4 hours, concentrated, taken up in water, washed several times with diethyl ether, acidified to pH 1 with concentrated hydrochloric acid and then extracted with diethyl ether and dried.

Yield: 99%

Melting point: 125° C.

Proton nuclear magnetic resonance spectrum (solvent $CDCl_3$): 6.7 ppm, 2H, 2d; 5.95 ppm, 2H, s; 4.3 ppm, 1H, t; 3.45 ppm, 2H, d.

Stage G 1-hydroxymethyl-3,4-methylenedioxybenzocyclobutene

Under a nitrogen atmosphere, 7.4 g of lithium aluminum hydride are added to 100 ml of diethyl ether and then 15 g of the compound prepared in Stage F, dissolved in 300 ml of diethyl ether, are added dropwise thereto. When the addition is complete, the mixture is refluxed for 3 hours. The excess hydride is hydrolysed, the mixture is filtered, the residue is washed several times with diethyl ether and the filtrate and washings are concentrated. The alcohol is obtained in the form of an oil.

Yield: 87%

Proton nuclear magnetic resonance spectrum (solvent $CDCl_3$): 6.65 ppm, 2H, 2d; 5.9 ppm, 2H, s; 3.9 ppm, 2H, m; 3.65 ppm, 1H, m; 3.25 ppm, 1H, dd; 2.9 ppm, 1H, dd; 1.5 ppm, 1H exchangeable.

Stage H 1-methyl-3,4-methylenedioxybenzocyclobutene tosylate 19 g of para-toluenesulphonyl chloride are added at 0° C. to 12.1 g of the alcohol obtained in the above Stage dissolved in 84 ml of pyridine. The mixture is stirred for 48 hours at room temperature, concentrated, taken up in water and filtered, and the residue is washed several times with water and then with 1N hydrochloric acid and dried.

Yield: 82%

Melting point: 102° C.

Proton nuclear magnetic resonance spectrum (solvent $DMSO-d_6$): 7.75 ppm, 2H, d; 7.45 ppm, 2H, d; 6.75 ppm, 1H, d; 6.55 ppm, 1H, d; 5.95 ppm, 2H, s; 4.25 ppm, 2H, m; 3.7 ppm, 1H, m; 3.3 to 3.1 ppm, 1H, 2d; 2.7 to 2.8 ppm, 1H, 2d; 2.4 ppm, 3H, s.

Stage I 4 g of the compound obtained in Stage H, 2.24 g of the compound obtained in Stage B of Example 6 and 1.7 ml of triethanolamine are refluxed in 40 ml of toluene for 24 hours. The reaction mixture is concentrated, taken up in ethyl acetate, washed with water and then extracted with 1N hydrochloric acid, and the extract is rendered basic with concentrated sodium hydroxide solution and extracted with methylene chloride. The extract is dried to yield ethyl N-(1-[(3,4-methylenedioxybenzocyclobuten-1-yl)-methyl]-piperid-4-yl)-N- methylcarbamate. 23.5 ml of a 2% solution of fumaric acid in ethanol are added to yield the desired salt.

Yield: 17%
Melting point: 138°–142° C.
Elemental analysis:

|     | Theory | Found |
| --- | --- | --- |
| C % | 59.73 | 59.45 |
| H % | 6.54 | 6.41 |
| N % | 6.06 | 5.82 |

EXAMPLE 29

N-{(1-(3,4-methylenedioxybenzocyclobuten-1-yl)-methyl]-piperid-4-yl}-N-methylpropionamide hydrochloride This compound was prepared in accordance with the process described in Stage I of Example 28 but using N-piperid-4-yln-methylpropionamide instead of methyl N-piperid-4-yl-N-methylcarbamate. Ethereal hydrogen chloride was used for the salt formation.

Yield: 36%
Melting point: 208°–211° C.
Elemental analysis:

|      | Theory | Found |       |
| ---  | ---    | ---   | ---   |
| C %  | 62.20  | 62.10 | 61.83 |
| H %  | 7.42   | 7.58  | 7.46  |
| N %  | 7.64   | 7.51  | 7.39  |
| Cl % | 9.66   | 9.39  | 9.36  |

EXAMPLE 30

N-{1-[(1,2-dihydro-2-oxo-1-phenyl-1,8-naphthyridin-3-yl)-methyl]-piperid-4-yl}-N-methylpropionamide This compound was prepared in accordance with the process described in Example 27 but using aniline instead of 2-fluoroaniline in Stage A.

Yield: 16.5%
Melting point: 181°–183° C.
Elemental analysis:

|     | Theory | Found |       |
| --- | ---    | ---   | ---   |
| C % | 71.26  | 71.57 | 71.53 |
| H % | 6.98   | 7.25  | 7.26  |
| N % | 13.85  | 14.12 | 14.25 |

EXAMPLE 31

N-(1-indan-2-ylpiperid-4-yl)-N-methylpropionamide

Stage A

Indanyl p-toluenesulphonate 47.4 g of tosyl chloride are added to 30 g of 2-indanol dissolved in 75 ml of pyridine which has been cooled to 0° C. The mixture is left at that temperature for 3 hours and then at room temperature for one night. The reaction solution is then poured onto 450 ml of 2.6N hydrochloric acid, filtered, and the residue washed with water to yield the desired compound.

Melting point: 117° C.
Proton nuclear magnetic resonance spectrum (solvent CDCl$_3$): 7.8 ppm, 2H, d; 7.35 ppm, 2H, d; 7.15 ppm, 4H, s; 5.3 ppm, 1H, m; 2.95 to 3.35 ppm, 4H, m; 2.5 ppm, 3H, s.

Stage B 4 g of the compound obtained in the above Stage, 2.95 g of the compound described in Stage C of Example 1, and 3 ml of N,N-diisopropylethylamine in 40 ml of toluene are mixed together and refluxed for 24 hours.

The reaction mixture is concentrated and taken up in diethyl ether, washed with water and extracted with hydrochloric acid.

The aqueous phase is rendered basic and extracted with diethyl ether. The extract is dried, concentrated and recrystallised from 7 ml of ethyl acetate.

Yield: 30%
Melting point 126°–129° C.
Elemental analysis:

|     | Theory | Found |       |
| --- | ---    | ---   | ---   |
| C % | 75.48  | 75.76 | 75.19 |
| H % | 9.15   | 8.96  | 9.19  |
| N % | 9.78   | 9.80  | 9.70  |

EXAMPLE 32

Ethyl N-{1-[[1,2-dihydro-2-oxo-1-(3-trifluoromethylphenyl)-1,8-naphthyridin-3-yl]-ethyl]-piperid-4-yl)-N-methylcarbamate hydrochloride

Stage A 1,2-dihydro-3-hydroxyethyl-2-oxo-1-(3-trifluoromethylphenyl)-1,8-naphthyridine 7.2 g of 60% sodium hydride are covered with 150 ml of benzene, then 31.5 g of 2-[(3-trifluorophenyl)-amino]-3-formylpyridine (prepared in accordance with the process described in Stages A–C of Example 27) and 31.25 g of γ-butyrolactone dissolved in 150 ml of benzene are added dropwise. The reaction is primed with a few drops of ethanol. The reaction mixture is left at room temperature for one night, hydrolysed with 50 ml of water and then the benzene is decanted off. The organic phase is washed with water. The aqueous phases are re-extracted with methylene chloride and the organic phases are combined and dried.

Yield: 50%
Melting point: 175° C.
Proton nuclear magnetic resonance spectrum (solvent CDCl$_3$): 8.4 ppm, 1H, dd; 7.95 ppm, 1H, dd; 7.8 to 7.65 ppm, 3H, m; 7.6 ppm, 1H, s broad; 7.5 ppm, 1H, dd; 7.2 ppm, 1H, dd; 3.95 ppm, 2H, d; 2.95 ppm, 2H, t; 2.7 ppm, 1H, t.

Stage B 3-chloroethyl-1,2-dihydro-2-oxo-1-(3-trifluoromethylphenyl)-1,8-naphthyridine 19.5 g of the alcohol prepared above are dissolved in 244 ml of methylene chloride. 13 ml of thionyl chloride are added dropwise thereto. The reaction mixture is refluxed for 3 hours and allowed to cool, then the methylene chloride is washed with water, then with 0.1N sodium hydroxide, dried and then the product is recrystallised from diisopropyl ether.

Yield: 78%
Melting point: 124° C.

Proton nuclear magnetic resonance spectrum (solvent CDCl₃): 8.3 ppm, 1H, dd; 7.9 ppm, 1H, dd; 7.65 ppm, 1H, s; 7.7 to 7.3 ppm, 4H, m; 7.1 ppm, 1H, m; 3.8 ppm, 2H, t; 3.05 ppm, 2H, t.

Stage C 3.5 g of the compound obtained in the above Stage, 1.85 g of the compound obtained in Stage B of Example 6 and 3.15 g of sodium carbonate are mixed in 60 ml of methyl isobutyl ketone and refluxed for 7 hours.

The reaction mixture is concentrated, taken up with water and with diethyl ether, and extracted with N hydrochloric acid. The extract is rendered basic with sodium hydroxide solution, concentrated and extracted with diethyl ether.

The oily base so obtained is dried and converted into a salt using 3.2N ethereal hydrogen chloride.

The hydrochloride is concentrated and recrystallised from ethyl acetate and then from ethanol.
Yield: 10%
Melting point: 220°–225° C.
Elemental analysis:

|  | Theory | Found | |
|---|---|---|---|
| C % | 57.94 | 57.79 | 57.40 |
| H % | 5.61 | 5.68 | 5.70 |
| N % | 10.39 | 10.26 | 10.32 |
| Cl % | 6.58 | 6.57 | 6.50 |

EXAMPLE 33

N-{1-[[1,2-dihydro-2-oxo-1-(3-trifluoromethylphenyl)-1,8-naphthyridin-3-yl]-ethyl]-piperid-4-yl}-N-methyl-propionamide hydrochloride.

This compound was prepared in accordance with the process described in Example 32 but replacing ethyl N-piperid-4-yl-N-methylcarbamate with N-piperid-4-yl-N-methylpropionamide in Stage C.
Yield: 10%
Melting point: 271°–274° C.
Elemental analysis:

|  | Theory | Found | |
|---|---|---|---|
| C % | 59.71 | 59.93 | 59.51 |
| H % | 5.78 | 5.75 | 5.90 |
| N % | 10.71 | 10.64 | 10.51 |
| Cl % | 6.78 | 6.71 | 6.81 |

EXAMPLE 34

N-{1-[(2,3-dihydrobenzofuran-2-yl)-methyl]-piperid-4-yl}-N-methylpropionamide hydrochloride 5.1 g of N-piperid-4-yl-N-methylpropionamide acetate, 90 ml of dimethylformamide and 6.3 ml of triethylamine are introduced into a 250 ml three-necked flask. 6.6 g of 2,3-dihydro-2-iodomethylbenzofuran are poured onto the mixture which is heated to 60°–65° C. This temperature is maintained for 15 hours. The reaction mixture is evaporated to dryness and the residue is taken up in ethyl acetate and extracted with 150 ml of N hydrochloric acid. The aqueous phase is rendered alkaline with sodium hydroxide in the presence of ethyl acetate. The organic phase is washed with water and dried over magnesium sulphate. The solvent is evaporated to yield a base in the form of a brown oil, which is converted into a salt with 3.8N ethereal hydrogen chloride to yield the desired compound.
Yield: 30%
Melting point: 153°–156° C.
Elemental analysis:

|  | Theory | Found |
|---|---|---|
| C % | 63.80 | 63.38 |
| H % | 8.03 | 8.03 |
| N % | 8.27 | 8.17 |
| Cl % | 10.46 | 10.06 |

EXAMPLE 35

N-{1-(benzocyclobuten-1-ylethyl)-piperid-4-yl)-N-methylpropionamide hydrochloride This compound was prepared from 1-bromoethylbenzocyclobutene and N-piperid-4-yl-N-methylpropionamide in accordance with the process described in Example 29.
Yield: 55%
Melting point: 224°–230° C.
Elemental analysis:

|  | Theory | Found |
|---|---|---|
| C % | 67.74 | 67.59 |
| H % | 8.68 | 8.66 |
| N % | 8.31 | 8.13 |
| Cl % | 10.52 | 10.45 |

EXAMPLE 36

1-[(1-benzocyclobuten-1-ylmethyl)-piperid-4-yl]-1-methyl-3-phenylurea hydrochloride 0.02 mol of phenyl isocyanate dissolved in 20 ml of diethyl ether is added to a solution of 1-benzocyclobuten-1-yl-4-methylaminopiperidine in diethyl ether while maintaining the temperature between 0° and 5° C. The reaction mixture is left at that temperature for 1 hour and then the resulting precipitate is filtered off to yield the desired urea. This compound is then dissolved in acetonitrile and converted into a salt with an appropriate amount of ethereal hydrogen chloride.
Yield: 80%
Melting point: >260° C.
Elemental analysis:

|  | Theory | Found | |
|---|---|---|---|
| C % | 68.47 | 68.38 | 68.08 |
| H % | 7.31 | 7.31 | 7.26 |
| N % | 10.89 | 11.06 | 11.10 |
| Cl % | 9.19 | 8.79 | 8.58 |

EXAMPLE 37

1-[(1-benzocyclobuten-1-ylmethyl)-piperid-4-yl]-3-ethyl-1-methylurea hydrochloride This compound was prepared in accordance with the process described in Example 36 but replacing phenyl isocyanate with ethyl isocyanate.
Yield: 65%
Melting point: >260° C.
Elemental analysis:

|  | Theory | Found | |
|---|---|---|---|
| C % | 63.98 | 63.99 | 63.63 |
| H % | 8.35 | 8.40 | 8.36 |
| N % | 12.44 | 12.57 | 12.67 |
| Cl % | 10.49 | 10.47 | 10.23 |

EXAMPLE 38

1-[(1-benzocyclobuten-1-ylmethyl)-piperid-4-yl]-3-benzyl-1-methylurea

This compound was prepared in accordance with the process described in Example 36 but replacing phenyl isocyanate with benzyl isocyanate.

Yield: 85%
Melting point: 148°–150° C.
Elemental analysis:

|  | Theory | Found | |
|---|---|---|---|
| C % | 76.00 | 75.56 | 75.92 |
| H % | 8.04 | 8.01 | 7.99 |
| N % | 11.56 | 11.55 | 11.69 |

EXAMPLE 39

N-[1-(benzocyclobuten-1-ylmethyl)-piperid-4-yl]-N-methylmethacrylamide hydrochloride 2.08 g of methacryloyl chloride are poured slowly, at room temperature, onto 4.6 g of 1-[(4-methylamino-piperid-1-yl)-methyl]-benyzocyclobutene (prepared in Stage E of Example 25) and 2.02 g of triethylamine in 50 ml of benzene.

The reaction mixture is left at room temperature for one night and then transferred to a dropping funnel and extracted with a normal HCl solution. The combined aqueous phases are rendered basic in the cold and then extracted with ether.

Flash chromatography (CH$_3$COOC$_2$H$_5$) yields 1.6 g of N-[1-(benzocyclobuten-1-ylmethyl)-piperid-4-yl]-N-methylmethacrylamide in the form of an oil.

Yield: 26%

Proton nuclear magnetic resonance spectrum (solvent CDCl$_3$): 7.3 to 7 ppm, 4H, m; 5.15 to 5 ppm, 2H, 2m; 4.5 and 3.7 ppm, 1H, 2m; 3.7 ppm, 1H, m; 3.4 ppm, 1H, dd; 3.1 ppm, 2H, d; 2.9 to 2.7 ppm, 2H, dd+m; 2.6 ppm, 1H, dd; 2.2 ppm, 2H, m; 2ppm, 3H, s; 2 to 1.5 ppm, 4H, m.

The hydrochloride of N-[1-(benzocyclobuten-1-ylmethyl)-piperid-4-yl]-N-methylmethacrylamide was obtained by adding the stoichiometric amount of 3.6 N ethereal hydrogen chloride to 1.6 g of the base prepared above dissolved in 10 ml of acetonitrile. 0.6 g of the desired compound is obtained after filtration and recrystallisation from methanol.

Yield: 34%
Melting point: >260° C. (K)
Elemental analysis:

|  | Theory | Found | |
|---|---|---|---|
| C % | 68.14 | 67.90 | 67.91 |
| H % | 8.13 | 8.06 | 8.12 |
| N % | 8.36 | 7.92 | 8.03 |
| Cl % | 10.59 | 10.87 | 10.53 |

EXAMPLE 40

N-[1-(benzocyclobuten-1-ylmethyl)-piperid-4-yl]-N-methylformamide 11 ml of acetic anhydride are added dropwise to a solution of 32 ml of 88% formic acid and 3 g of 1-[(4-methylaminopiperid-1-yl)-methyl]-benzocyclobutene (cf. Stage E of Example 25) that has been preheated to 40° C.

The reaction mixture is stirred for one night, and then evaporated, taken up in iced water, rendered basic in the cold and extracted with ether. Evaporation and recrystallisation from 15 ml of diisopropyl ether yield 5.3 g of N-[1-(benzocyclobuten-1-ylmethyl)-piperid-4-yl]-N-methylformamide.

Yield: 48%
Melting point: 86°–88° C.
Elemental analysis:

|  | Theory | Found | |
|---|---|---|---|
| C % | 74.38 | 74.21 | 74.34 |
| H % | 8.58 | 8.57 | 8.63 |
| N % | 10.84 | 10.79 | 10.68 |

EXAMPLE 41

(R,S)-2-oxapropyl N-[1-(benzocyclobuten-1-ylmethyl)-piperid-4-yl]-N-methylcarbamate hydrochloride

Stage A

Proceeding as described in Stage B of Example 1 starting from 1-benzyl-4-methylaminopiperidine (described in Stage A of Example 1) and

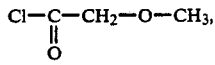

2-oxapropyl N-(1-benzylpiperid-4-yl)-N-methylcarbamate is obtained.

Yield: 87%

Proton nuclear magnetic resonance spectrum (solvent CDCl$_3$): 7.3 ppm, 5H, m; 4.5 and 3.5 ppm, 1H, 2m ; 4.10 and 4 ppm, 2H, 2s; 3.5 ppm, 2H, m; 3.4 ppm, 3H, s; 3 ppm, 2H, m; 2.8 ppm, 3H, s; 2.35 to 1.5 ppm, 6H, m.

Stage B 22 g of the base obtained above in 220 ml of ethanol and 4.8 ml of acetic acid are hydrogenated under a pressure of 5 kg of hydrogen at 50° C. in the presence of 2.2 g of palladium hydroxide. The catalyst is then filtered off, the solution is evaporated and the residue is taken up in 500 ml of methylene chloride and rendered basic in the cold with 60 ml of 20% sodium hydroxide solution. Decanting, drying and evaporation yield 9.3 g of 2-oxapropyl N-(piperid-4-yl)-N-methylcarbamate in the form of an oil.

Yield: 62%

Proton nuclear magnetic resonance spectrum (solvent CDCl$_3$): 4.55 to 3.6 ppm, 1H, 2m; 4.1 ppm, 2H, 2s; 2.45 ppm, 3H, 2s; 3.2 ppm, 2H, m; 2.85 ppm, 3H, 2s; 2.75 ppm, 2H, m; 1.9 to 1.55 ppm, 4H, m; 3.8 ppm, 1H exchanged with D$_2$O, s.

Stage C 1.8 g of 2-oxapropyl N-(piperid-4-yl)-N-methylcarbamate obtained above, 1.1 g of triethylamine and 2.8 g of 1-hydroxymethylbenzocyclobutane tosylate in 50 ml of toluene are refluxed for one night with stirring.

The reaction mixture is evaporated, taken up in ether and extracted with a normal HCl solution.

The aqueous phases are rendered basic in the cold and extracted with ethyl acetate to yield 1.6 g of 2-oxapropyl N-[1-(benzocyclobuten-1-ylmethyl)-piperid-4-yl]-N-methylcarbamate.

Yield: 14%

Proton nuclear magnetic resonance spectrum (solvent CDCl$_3$): 7.25 to 7 ppm, 4H, m; 4.6 to 4.4 and 3.7 to 3.5 ppm, 1H, m; 4.1 ppm, 2H, s; 3.7 ppm, 1H, m; 3.5 to 3.2 ppm, 4H, s+m; 3 to 1.5 ppm, 12H, s+5m; 3.1 ppm, 2H, m.

Stage D 2-oxapropyl N-[1-(benzocyclobuten-1-ylmethyl)-piperid-4-yl]-N-methylcarbamate hydrochloride is obtained by adding the stoichiometric amount of 3N HCl in ether to 1.4 g of the base prepared in Stage C in 5 ml acetonitrile.

After filtration and drying 1 g of the desired hydrochloride is obtained.

Yield: 77%

Melting point: 204°–° C. (K)

Elemental analysis:

|      | Theory | Found |             |
|------|--------|-------|-------------|
| C %  | 63.80  | 63.52 | corrected   |
| H %  | 8.03   | 7.87  | for 0.7%    |
| N %  | 8.27   | 8.18  | H$_2$O      |
| Cl % | 10.46  | 10.38 |             |

EXAMPLE 42

(R,S)-vinyl N-[1-(benzocyclobuten-1-ylmethyl)-piperid-4-yl]-N-methylcarbamate hydrochloride Proceeding as described in Example 39 starting from 3 g of 1-[(4-methylaminopiperid-1-yl)-methyl]-benzocylobutene (prepared in Stage E of Example 25) and vinyl chloroformate, (R,S)-vinyl N-[1-(benzyocyclobuten-1-ylmethyl)-piperid-4-yl]-N-methylcarbamate is obtained, which is dissolved in 5 ml of acetonitrile and converted into a salt with a 3.6N HCl solution in ether to yield 1.3 g of (R,S)-vinyl N-[1-(benzocyclobuten-1-ylmethyl)-piperid-4-yl]-N-methylcarbamate hydrochloride.

Yield: 30%

Melting point: 232°–234° C.

Elemental analysis:

|      | Theory | Found |       |
|------|--------|-------|-------|
| C %  | 64.18  | 63.89 | 63.80 |
| H %  | 7.48   | 7.34  | 7.77  |
| N %  | 8.32   | 8.29  | 8.17  |
| Cl % | 10.52  | 10.82 | 10.64 |

EXAMPLE 43

Isobutyl N-[1-(indan-2-yl)-piperid-4-yl]-N-methylcarbamate fumarate

A mixture of 3.71 g of isobutyl N-(piperid-4-yl)-N-methylcarbamate (prepared in Example 15), 4.9 ml of triethylamine, 50 ml of toluene and 5 g of indan-2-yl p-toluenesulphonate (prepared in accordance with Stage A of Example 31) is refluxed for 24 hours.

The precipitate is filtered off and washed several times with toluene. The washings and filtrate are then washed several times with water, dried and concentrated. The resulting oil is taken up in a 2% solution of fumaric acid in ethanol (mol per mol). Concentration and recrystallisation from 10 ml of ethanol yield isobutyl N-[1-(indan-2-yl)-piperid-4-yl]-N-methylcarbamate fumarate.

Yield: 14%

Melting point: 230°–234° C. with sublimation towards 180°–185° C.

Elemental analysis:

|     | Theory | Found |       |
|-----|--------|-------|-------|
| C % | 64.55  | 64.79 | 64.67 |
| H % | 7.67   | 7.71  | 7.62  |
| N % | 6.27   | 6.11  | 6.18  |

EXAMPLE 44

Propyl N-[1-(indan-2-yl)-piperid-4-yl]-N-methylcarbamate

A mixture of 3.47 g of propyl N-(piperid-4-yl)-N-methylcarbamate (prepared in Example 9), 4.9 ml of triethylamine, 50 ml of toluene and 5 g of indan-2-yl p-toluenesulphonate (prepared according to Stage A of Example 31) is refluxed for 24 hours.

100 ml of water are then added to this reaction mixture and, after decanting, the organic phase is extracted with a normal HCl solution. The acidic aqueous phase is then rendered basic with a normal sodium hydroxide solution and subsequently extracted with CH$_2$Cl$_2$ and dried over MgSO$_4$. The resulting solid is recrystallised from 10 ml of diisopropyl ether.

Yield: 42%

Melting point: 73°–76° C.

Elemental analysis:

|     | Theory | Found |
|-----|--------|-------|
| C % | 72.12  | 71.76 |
| H % | 8.92   | 8.79  |
| N % | 8.85   | 9.04  |

TABLE I
COMPOUNDS OF THE GENERAL FORMULA I $$R-(CH_2)_m-K-(CH_2)_p-L \quad (I)$$

where L = $\begin{array}{c} R_1 \\ | \\ -N-C-W-R_2 \\ \phantom{-N-}\| \\ \phantom{-N-}O \end{array}$

| EXAMPLE | R | m | K | p | L | NMR Spectrum (solvent) |
|---|---|---|---|---|---|---|
| 1 | 2-methyl-4H-chromen-4-one | 1 | 4-piperidinyl | 0 | $-N-CH_3$ / $O=C-C_2H_5$ | $^1$H NMR (CDCl$_3$) salt 8.1 ppm, 1H, dd; 7.5 to 7.7 ppm, 2H, m; 7.4 ppm, 1H, m; 6.7 ppm, 1H, s; 4.8 ppm, 1H, m; 4.3 ppm, 2H, s; 3.7 ppm, 2H, d; 3.2 ppm, 2H, t; 2.9 ppm, 3H, s; 2.5 to 2.9 ppm, 2H, m; 2.3 ppm, 2H, q; 1.8 ppm, 2H, m; 1.1 ppm, 3H, t; 13.15 ppm, 1H exchangeable. |
| 2 | 2-methyl-4H-chromen-4-one | 1 | 4-piperidinyl | 0 | $-N-CH_3$ / $O=C-C_3H_7$ | $^1$H NMR (CDCl$_3$) base 8.2 ppm, 1H, dd; 7.7 ppm, 1H, td; 7.45 ppm, 2H, m; 6.5–6.45, 1H, 2s; 4.55–3.6 ppm, 1H, 2m; 3.55–3.5, 2H, 2s; 3.1 ppm, 2H, m; 2.9 to 2.85 ppm, 3H, 2s; 2.3 ppm, 4H, m; 1.5 to 1.85 ppm, 6H, m; 1 ppm, 3H, t |
| 3 | 2-methyl-4H-chromen-4-one | 1 | 4-piperidinyl | 0 | $-N-CH_3$ / $O=C-CH_3$ | $^1$H NMR (CDCl$_3$) base 8.2 ppm, 1H, dd; 7.7 ppm, 1H, td; 7.45 ppm, 2H, m; 6.45 ppm, 1H, 2s; 4.5+3.6 ppm, 1H, 2m; 3.55 ppm, 2H, 2s; 3.1 ppm, 2H, m; 2.9 to 2.85 ppm, 3H, 2s; 2.35 ppm, 2H, m 2.1 ppm, 2s; 2.1 to 1.5 ppm, 4H, m |
| 4 | 2-methyl-4H-chromen-4-one | 1 | 4-piperidinyl | 0 | $-N-C_2H_5$ / $O=C-C_2H_5$ | $^1$H NMR (CDCl$_3$) salt 8.05 ppm, 1H, d; 7.95 ppm, 1H, t; 7.70 ppm 1H, d; 7.55 ppm, 2H, m; 6.7 ppm, 1H, 2s; 4.4 ppm, 2H, s; 4.4 to 4 ppm, 1H, 2m; 3.6 ppm, 2H, m; 3.25 ppm, 4H, m; 2.35 ppm, 4H, m; 1.8 ppm, 2H, m; 1.15 to 1.05 ppm, 6H, 1+2t; 11.75 ppm, 1H exchangeable |

TABLE I-continued
COMPOUNDS OF THE GENERAL FORMULA I $$R-(CH_2)_m-\underset{K}{\boxed{\begin{array}{c}(CH_2)_n\\ \diagup\diagdown\\ N\end{array}}}-(CH_2)_p-\underset{L}{\boxed{\begin{array}{c}R_1\\ |\\ N-C-W-R_2\\ \|\\ O\end{array}}}$$ (I)

| EXAMPLE | R | m | K | p | L | NMR Spectrum (solvent) |
|---|---|---|---|---|---|---|
| 5 | chromon-2-yl (2-methyl-4H-chromen-4-one) | 2 | 4-piperidyl | 0 | —N(CH₃)—C(=O)—O—C₂H₅ | ¹H NMR (DMSO-d₆) salt 8.05 ppm, 1H, d; 7.8 ppm, 1H, t; 7.6 ppm 1H, d; 7.5 ppm, 1H, t; 6.4 ppm, 1H, s; 4.6+4 ppm, 1H, 2m; 3.55 ppm, 4H, m; 3.2 ppm, 4H, m; 2.8+2.6 ppm, 3H, 2s; 2.4+2.3 ppm, 2H, 2q; 2.10 ppm, 2H, m; 1.7 ppm, 2H, m; 1 ppm, 3H, 2t; 11.2 ppm, 1H exchangeable |
| 6 | chromon-2-yl | 1 | 4-piperidyl | 0 | —N(CH₃)—C(=O)—O—C₂H₅ | ¹H NMR (DMSO-d₆) salt 8.05 ppm, 1H, dd; 7.85 ppm, 1H, td; 7.7 ppm 1H, d; 7.55 ppm, 1H, t; 6.75 ppm, 1H, 2s; 4.4 ppm, 2H, s; 4.15 ppm, 1H, m; 4.05 ppm, 2H, q; 3.6 ppm, 2H, m; 3.3 ppm, 2H, m; 2.75 ppm, 3H, s; 2.3 ppm, 2H, m; 1.75 ppm, 2H, m; 1.2 ppm, 3H, t; 11.7 ppm, 1H exchangeable |
| 7 | chromon-2-yl | 1 | 4-piperidyl | 0 | —N(CH₃)—C(=O)—CH(CH₃)₂ | ¹H NMR (DMSO-d₆) salt 8.05 ppm, 1H, d; 7.9 ppm, 1H, t; 7.7 ppm 1H, d; 7.55 ppm, 1H, t; 6.75 ppm, 1H, 2s; 4.6+4.1 ppm, 1H, 2m; 4.4 ppm, 2H, s; 3.6 ppm, 2H, m; 3.3 ppm, 2H, m; 2.9+2.7 ppm 3H, 2s; 2.85 ppm, 1H, s; 2.35 ppm, 2H, m; 1.7 ppm, 2H, m; 1 ppm, 6H, d; 12–11.5 ppm, 1H exchangeable |
| 8 | bicyclo[4.2.0]benzocyclobutenyl | 1 | 4-piperidyl | 0 | —N(CH₃)—C(=O)—O—CH₃ | ¹H NMR (CDCl₃) base 7.3 to 7 ppm, 4H, m; 4.4 ppm, 1H, m; 4.2 ppm, 1H, m; 3.8 to 3.4 ppm, 6H, m; 3.3 to 3.0 ppm, 2H, m; 3 to 2.6 ppm, 8H, m; 1.85 ppm, 2H, m; 13 to 12.7 ppm, 1H exchangeable |

TABLE I-continued

COMPOUNDS OF THE GENERAL FORMULA I $$R-(CH_2)_m-\underset{K}{\boxed{\overset{(CH_2)_n}{N}}}-(CH_2)_p-\underset{L}{\boxed{N\underset{R_1}{\overset{R_1}{\underset{|}{-}}}\underset{O}{\overset{}{C}}-W-R_2}}\quad (I)$$

| EXAMPLE | R | m | K | p | L | NMR Spectrum (solvent) |
|---|---|---|---|---|---|---|
| 9 | benzocyclobutenyl | 1 | 4-piperidinyl | 0 | —N(CH₃)—C(O)—O—C₃H₇ | ¹H NMR (CDCl₃) salt 7.4 to 7 ppm, 4H, m; 4.4 ppm, 1H, m; 4.3 to 3.9 ppm, 4H, m; 4.4 ppm, 1H, m; 3H, m+m; 3.3 to 3 ppm, 2H, m±m; 2.85 ppm 3H, s; 3 to 2.5 ppm, 3H, m±m; 2 to 1.5 ppm, 6H, m+m+m; 0.95 ppm, 3H, t; 12.75 ppm, 1H exchangeable |
| 10 | benzocyclobutenyl | 1 | 4-piperidinyl | 0 | —N(CH₃)—C(O)—O—C₂F₅ | ¹H NMR (DMSO-d6) salt 7.3 to 7 ppm, 4H, m; 4.5 et 4.2 ppm, 1H, 2m; 3.9 ppm, 1H, m; 3.5 ppm, 1H, m; 3.5 to 3 ppm, 7H, 4m; 2.8 and 3 ppm 3H, 2s; 2.1 to 2.6 ppm, 2H, m; 1.85 ppm, 2H, m; 10.75 ppm, 1H exchangeable |
| 11 | benzocyclobutenyl | 1 | 4-piperidinyl | 0 | —N(CH₃)—C(O)—O—C(CH₃)₃ | ¹H NMR (CDCl₃ + DMSO) 7.3 to 7 ppm, 4H, m; 4.50 to 4.05 ppm 2H, m; 2.8 ppm, 3H, s; 1.85 ppm, 2H, d 1.45 ppm, 9H, s; 3.8 to 2.4 ppm, 10H, m; 13 to 12 ppm, 1H exchangeable |
| 12 | benzocyclobutenyl | 1 | 4-piperidinyl | 0 | —N(CH₃)—C(O)—phenyl | ¹H NMR (DMSO-d6) 7.5 to 7 ppm, 9H, m; 4.3 ppm, 1H, m; 4 ppm, 1H, m; 3.7 to 3 ppm, 8H, 4m; 2.9 ppm, 3H, m; 2.5 to 2.2 ppm, 2H, m; 1.9 ppm, 2H, m; 10.9 ppm, 1H exchangeable |
| 13 | benzocyclobutenyl | 1 | 4-piperidinyl | 0 | —N(C₂H₅)—C(O)—O—C₂H₅ | ¹H NMR (DMSO-d6) 7.2 ppm, 4H, m; 4.2 to 3.3 ppm, 4H, m; 3.7 to 3 ppm, 10H, m; 1.8 ppm, 4H, m; 1.2 ppm, 3H, t; 1.05 ppm, 3H, t; 10.9 ppm, 1H exchangeable |

TABLE I-continued
COMPOUNDS OF THE GENERAL FORMULA I $$R-(CH_2)_m-\boxed{\underset{K}{\overset{(CH_2)_n}{N}}}-(CH_2)_p-\boxed{\underset{L}{\overset{R_1}{N}-\overset{O}{\underset{\|}{C}}-W-R_2}} \quad (I)$$

| EXAMPLE | R | m | K | p | L | $^1$H NMR Spectrum (solvent) |
|---|---|---|---|---|---|---|
| 14 | benzocyclobutenyl | 1 | 4-piperidinyl | 0 | $-N(C_2H_5)-C(=O)-O-CH_3$ | $^1$H NMR (DMSO-$d_6$) salt 7.3 to 7 ppm, 4H, m; 4.1 to 3.8 ppm, 1H+1H m+m; 3.6 ppm, 3H, s; 3.6 to 3 ppm, 1H+1H+2H+4H+2H, m+m+m+m+m; 2.3 ppm, 2H, m; 1.75 ppm, 2H, m, 1.1 ppm, 3H, t; 10.95 ppm, 1H exchangeable |
| 15 | benzocyclobutenyl | 1 | 4-piperidinyl | 0 | $-N(CH_3)-C(=O)-O-CH_2-CH(CH_3)_2$ | $^1$H NMR (DMSO-$d_6$) salt 7.15 ppm, 4H, m; 6.6 ppm, 2H, s; 4 to 3.6 ppm, 2H, m; 3.8 ppm, 2H, d; 3.3 ppm, 1H, dd; 3.15 ppm, 2H, m; 3 to 2.6 ppm, 3H, m; 2.75 ppm, 3H, s; 2.3 ppm, 2H, m; 2 to 1.7 ppm, 3H, m; 1.6 ppm, 2H, m; 0.9 ppm, 6H, d |
| 16 | benzocyclobutenyl | 1 | 4-piperidinyl | 0 | $-NH-C(=O)-C_2H_5$ | $^1$H NMR (DMSO-$d_6$) salt 8.15 and 8.05 ppm, 1H, 2d; 7.1 to 7.3 ppm, 4H, m; 4.0 ppm, 1H, m; 3.75 ppm, 1H, m 3.6 to 2.9 ppm, 8H, m; 2.3 to 2.0 ppm, 2H, q; 2.1 to 1.7 ppm, 4H, m; 1 ppm, 3H, 2t; 11.05 and 10.8 ppm 1H exchangeable |
| 17 | benzocyclobutenyl | 1 | 4-piperidinyl | 0 | $-N(CH_3)-C(=O)-O-C_2H_5-O-CH_3$ | $^1$H NMR (CDCl$_3$) salt 7.3 to 7, 4H, m; 4.5 to 4.1 ppm, 4H, m+m+m; 3.8 to 3.3 ppm, 8H, m+m+m+s+m; 3.3 a 3 ppm, 3H, m 3 to 2.6 ppm, 7H, s+m+m; 1.8 ppm 2H, m; 12.8 ppm, 1H exchangeable |
| 18 | benzocyclobutenyl | 1 | 4-piperidinyl | 0 | $-N(CH_3)-C(=O)-cyclohexyl$ | $^1$H NMR (DMSO-$d_6$) salt 7.2 ppm, 4H, m; 4.55 ppm, 1H, m; 4.3 to 3.8 ppm, 2H, m+m; 3.7 to 2.9 ppm, 8H, m+m+m; 2.75 ppm, 3H, s; 2.2 ppm, 2H, m; 1.9 to 1.2 ppm, 12H, m; 10.95 ppm, 1H exchangeable |

TABLE I-continued
COMPOUNDS OF THE GENERAL FORMULA I $$R-(CH_2)_m-K-(CH_2)_p-L \quad (I)$$

where L = $-N(R_1)-C(=O)-W-R_2$

| EXAMPLE | R | m | K | p | L | NMR Spectrum (solvent) |
|---|---|---|---|---|---|---|
| 19 | benzocyclobutenyl | 1 | 4-piperidinyl | 0 | $-N(CH_3)-C(=O)-O-CH_2-$phenyl | $^1$H NMR (DMSO-d$_6$) salt 7.6 to 7 ppm, 9H; 5.1 ppm, 2H, s; 4.2 ppm, 1H, m; 3.95 ppm, 1H, m; 3.8 to 3 ppm, 8H, m; 2.8 ppm, 3H, s; 2.25 ppm, 2H, m; 1.8 ppm, 2H, d; 11.2 ppm 1H exchangeable |
| 20 | 1-methyl-benzocyclobutenyl | 1 | 4-piperidinyl | 0 | $-N(CH_3)-C(=O)-C_2H_5$ | $^1$H NMR (CDCl$_3$) salt 7.4 to 7.0 ppm, 4H +1 echangeable, m; 4.8 ppm, 1H, m; 3.9 to 2.6 ppm, 11H, m; 2.3 ppm, 2H, q; 1.8 ppm, 3H, s; 1.9 to 1.5 ppm, 4H, m; 1.15 ppm, 3H, t |
| 21 | benzocyclobutenyl | 1 | 4-piperidinyl | 0 | $-N(C_2H_5)-C(=O)-CH_3$ | $^1$H NMR (CDCl$_3$) salt 7.25 ppm, 2H, m; 7.1 ppm, 2H, m; 4.8 ppm, 1H, m; 4.2 ppm, 1H, m; 3.8–3.1 ppm, 8H, m 2.9–2.7 ppm, 4H, m; 2.15 ppm, 3H, s; 1.9 ppm, 2H, m 1.25 ppm, 3H, t; 12.8 ppm, 1H exchangeable |
| 22 | benzocyclobutenyl | 1 | 4-piperidinyl | 0 | $-N(CH_3)-C(=O)-C_2H_5$ | $^1$H NMR (CDCL$_3$) salt 7.25 ppm, 2H, m; 7.1 ppm, 2H, m; 4.85 ppm, 1H, m; 4.2 ppm, 1H, m; 3.75 ppm, 2H, m; 3.6 ppm, 1H, dd; 3.5 ppm, 1H, dd; 3.25 ppm, 1H, dd; 3.15 ppm, 1H, dd; 3.0 to 2.6 ppm, 4H, m; 3.0 ppm, 3H, s; 2.35 ppm, 2H, q; 1.8 ppm, 2H, m; 1.15 pm, 3H, t; 12.75 ppm, 1H exchangeable |

TABLE I-continued
COMPOUNDS OF THE GENERAL FORMULA I $$R-(CH_2)_m-\underset{K}{\boxed{N-(CH_2)_p}}-\underset{L}{\boxed{\overset{R_1}{\underset{|}{N}}-\overset{O}{\underset{\|}{C}}-W-R_2}} \quad (I)$$

| EXAMPLE | R | m | K | p | L | NMR Spectrum (solvent) |
|---|---|---|---|---|---|---|
| 23 | phenyl | 1 | 4-piperidinyl | 0 | —N—CH₃ / O=C—O—C₂H₅ | ¹H NMR (CDCl₃) salt 7.25 ppm, 2H, m; 7.1 ppm, 2H, m; 4.4 ppm, 1H, m; 4.15 ppm, 3H, m+q 3.75 ppm, 2H, m; 3.6 ppm, 1H, dd; 3.3 ppm, 1H, dd; 3.25 ppm, 1H, dd; 2.85 ppm, 3H, s; 3.05–2.6 ppm, 4H, m; 1.85 ppm, 2H, m; 1.3 ppm, 3H, t; 11.7 ppm, 1H exchangeable |
| 24 | phenyl | 1 | 4-piperidinyl | 0 | —N—CH₃ / O=C—C₃H₇ | ¹H NMR (CDCl₃) salt 7.25 ppm, 2H, m; 7.1 ppm, 2H, m; 4.85 ppm, 1H, m; 4.2 ppm, 1H, m; 3.8–3.1 ppm, 6H, m; 3.0 ppm, 3H, s; 3.05–2.6 ppm, 4H, m; 2.3 ppm, 2H, t; 1.8 ppm, 2H, m; 1.7 ppm, 2H, s; 1.0 ppm, 3H, t; 12.7 ppm, 1H exchangeable |
| 25 | phenyl | 1 | 4-piperidinyl | 0 | —N—CH₃ / O=C—O—CH₂—CH=CH₂ | ¹H NMR (CDCl₃) salt 7.3 to 7.1 ppm, 4H, m; 6.1 to 5.8 ppm, 1H, m; 5.4 to 5.1 ppm, 2H, m; 4.5 ppm, 2H, d; 4.2 ppm, 1H, m; 3.95 ppm, 1H, m; 3.7 to 3 ppm, 2H, m + 1H, dd + 2H, m + 2H, m + 1H, dd + 2.75 ppm, 3H, s 2.4 to 2.1 ppm, 2H, m; 1.75 ppm, 2H, m; 10.9 ppm, 1H exchangeable |
| 26 | phenyl | 1 | 4-piperidinyl | 0 | —N—CH₃ / O=C—CH=CH₂ | ¹H NMR (DMSO-d₆) salt 7.2 ppm, 4H, m; 6.8 ppm, 1H, m; 6.1 to 5.7 ppm, 2H, 2d; 4.65 to 4.2 ppm, 1H, 2m; 3.95 ppm, 1H, m; 3.7 to 3 ppm, 2H + 1H + 2H, m+dd+m+m; 2.75 to 2.5 ppm, 3H, 2s; 2.25 ppm, 2H, m; 1.7 ppm, 2H, m; 10.8 ppm, 1H exchangeable |

TABLE I-continued

COMPOUNDS OF THE GENERAL FORMULA I

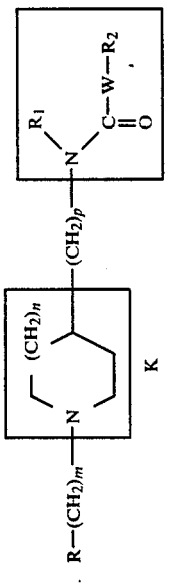

| EXAMPLE | R | m | K | p | L | NMR Spectrum (solvent) |
|---|---|---|---|---|---|---|
| 27 | [3-methyl-1-(2-fluorophenyl)-2-oxo-1,2-dihydro-1,8-naphthyridin-4-yl] | 1 | 4-piperidyl | 0 | —N—CH₃ / O=C—C₂H₅ | ¹H NMR (CDCl₃) base 8.4 ppm, 1H, dd; 7.95 ppm, 1H, dd; 7.25 ppm, 1H, 2s; 7.45 ppm, 1H, m; 7.4 to 7.1 ppm, 4H, m; 4.55 and 3.6 ppm, 1H, 2s; 3.56 ppm, 2H, s; 3.05 ppm, 2H, m; 2.8 ppm, 3H, s; 2.5 to 2.1 ppm, 2H, m+2H, q; 2.1 to 1.5 ppm, 4H, m; 1.1 ppm, 3H, 2t |
| 28 | benzodioxole | 1 | 4-piperidyl | 0 | —N—CH₃ / O=C—O—C₂H₅ | ¹H NMR (CDCl₃ + DMSO-d₆) salt 6.8 ppm, 2H, s; 6.7 ppm, 1H, d; 6.55 ppm, 2H, s; 6.7 ppm, 1H, s; 6.7 ppm, 1H, d; 6.55 ppm, 1H, d; 5.9 ppm, 2H, s; 4.15 ppm, 3H, q; 3.8 ppm, 1H, m; 3.6–3.2 ppm, 3H, m; 3.15–2.7 ppm, 3H, m; 2.75 ppm, 3H, s; 2.5 ppm, 2H, m; 2.05 ppm, 2H, 1.75 ppm, 2H m; 1.25 ppm, 3H, t; 7.3 ppm, 2H exchangeable |
| 29 | benzodioxole | 1 | 4-piperidyl | 0 | —N—CH₃ / O=C—C₂H₅ | ¹H NMR (DMSO-d₆) salt 6.8 ppm, 2H, d; 6.7 ppm, 1H, d; 6 ppm, 2H, 2s; 4.6 to 3.5 ppm, 1H, 2m; 3.95 ppm, 1H, m; 3.7 ppm, 8H, m; 2.8 ppm, 3H, 2s, 2.4 a 2 ppm, 2H+2H, q+m; 1.9 to 1.5 ppm, 2H, m; 1 ppm, 3H, t; 11.5 to 11 ppm, 1H exchangeable |

TABLE I-continued

COMPOUNDS OF THE GENERAL FORMULA I $$R-(CH_2)_m-K-(CH_2)_p-L \quad (I)$$

where L is:

$$\begin{array}{c} R_1 \\ | \\ -N-C-W-R_2 \\ \phantom{-N-}\| \\ \phantom{-N-}O \end{array}$$

and K is a ring containing $(CH_2)_n$ with N.

| EXAMPLE | R | m | K | p | L | NMR Spectrum (solvent) |
|---------|---|---|---|---|---|------------------------|
| 30 | 3-methyl-1-phenyl-[1,8]naphthyridin-2(1H)-one | 1 | 4-piperidinyl | 0 | —N—CH₃<br>O=C—C₂H₅ | ¹H NMR (DMSO-d₆) base 8.4 ppm, 1H, d; 7.95 ppm, 1H, dd; 7.8 ppm, 1H, d; 7.5 ppm, 3H, m; 7.25 ppm, 2H, m; 7.1 ppm, 1H, m; 4.55 and 3.55 ppm, 1H, m; 3.5 ppm 2H, s; 3.05 ppm, 2H, m; 2.9 ppm 3H, s; 2.1–2.4 ppm, 2H, m + 2H, d; 1.5 to 2.1 ppm, 4H, m; 1.15 ppm, 3H, td |
| 31 | 2-methyl-indane | 0 | 4-piperidinyl | 0 | —N—CH₃<br>O=C—C₂H₅ | ¹H NMR (CDCl₃) base 7.15 ppm, 4H, m; 4.55 to 3.55 ppm, 1H, 2m; 3.2 to 3 ppm, 5H, m; 3.0 to 2.9 ppm, 2H, d; 3.85 ppm, 3H, d; 2.35 ppm, 2H, q; 2.2 ppm, 2H, q; 2.05 a 1.5 ppm, 4H, m; 1.15 ppm, 3H, dd |
| 32 | 3-methyl-1-(3-trifluoromethylphenyl)-[1,8]naphthyridin-2(1H)-one | 2 | 4-piperidinyl | 0 | —N—CH₃<br>O=C—O—C₂H₅ | ¹H NMR (DMSO-d₆) salt 8.4 ppm, 1H, d; 8.15 ppm, 1H, d; 8.1 ppm, 1H, s; 7.6 to 7.9 ppm, 4H, m; 7.35 ppm, 1H, dd; 4.15 ppm, 1H, m; 4.05 ppm, 2H, q; 3.6 ppm, 2H, m; 2.9 to 3.5 ppm, 2H, m; 2.7 ppm, 3H, s; 2.15 ppm, 2H, m; 1.75 ppm, 2H, m; 1.2 ppm, 3H, t; 10.6 ppm, 1H exchangeable |

TABLE I-continued
COMPOUNDS OF THE GENERAL FORMULA I

| EXAMPLE | R | m | K | p | L | NMR Spectrum (solvent) |
|---|---|---|---|---|---|---|
| 33 | 3-methyl-1-(3-trifluoromethylphenyl)-1,8-naphthyridin-2(1H)-one | 2 | 4-piperidinyl | 0 | —N(CH₃)—C(O)—C₂H₅ | ¹H NMR (CDCl₃) salt 8.45 ppm, 1H, dd; 8.00 ppm, 1H, s; 7.95 ppm, 1H, m; 7.65 to 7.85 ppm, 2H, m; 7.55 ppm, 1H, s; 7.5 ppm, 1H, d; 7.2 ppm, 1H, dd; 4.8 ppm, 1H, m; 3.7 ppm, 2H, d; 3.15 to 3.5 ppm 4H, m; 2.95 ppm, 3H, s 2.85 ppm, 2H, d; 2.45 to 2.7 ppm, 2H, m 2.35 ppm, 2H, g; 1.8 ppm, 2H, d; 1.1 ppm, 3H, t; 12.5 ppm, 1H exchangeable |
| 34 | 2,3-dihydrobenzofuran-2-yl | 1 | 4-piperidinyl | 0 | —N(CH₃)—C(O)—C₂H₅ | ¹H NMR (CDCl₃) salt 7.15 ppm, 2H, m; 6.9 ppm, 1H, t; 6.8 ppm, 1H, d; 5.55 ppm, 1H, m; 4.85 ppm, 1H, m; 4.10 ppm, 1H, m; 3.65–3.3 ppm, 3H, m; 3.25–2.8 ppm, 4H, m; 2.95 ppm, 3H, s; 2.65 ppm, 2H, m; 2.35 ppm, 2H, g; 1.8 ppm, 2H, m; 1.15 ppm, 3H, t; 12.9 ppm, 1H exchangeable |
| 35 | bicyclo[4.2.0]octa-1,3,5-trien-7-yl | 2 | 4-piperidinyl | 0 | —N(CH₃)—C(O)—C₂H₅ | ¹H NMR (CDCl₃) salt 7.2+7.05 ppm, 2H+2H, m+m; 4.8 ppm, 1H, m; 3.6 ppm, 3H, m; 3.4 ppm, 1H, dd; 3.1 ppm, 2H, m; 2.9 ppm, 3H, s; 2.45 to 2.55 ppm, 5H, m; 2.35 ppm, 4H, g+m; 1.75 ppm, 2H, m; 1.1 ppm, 3H, t; 12.5 ppm, 1H exchangeable |
| 36 | bicyclo[4.2.0]octa-1,3,5-trien-7-yl | 1 | 4-piperidinyl | 0 | —N(CH₃)—C(O)—NH—C₆H₅ | ¹H NMR (DMSO-d₆) salt 7.5 ppm, 2H, d 7.3 to 7.1 ppm, 6H, m + 1H exchangeable; 6.95 ppm, 1H, t; 3.95 ppm, 2H, m; 3.7 to 2.9 ppm, 8H, m; 2.85 ppm, 3H, s; 2.25 to 13.75 ppm, 4H, m; 8.4 ppm, 1H exchangeable |

TABLE I-continued
COMPOUNDS OF THE GENERAL FORMULA I $$R-(CH_2)_m-\underset{K}{\boxed{N}}-(CH_2)_p-\underset{L}{\boxed{\underset{C=O}{\overset{R_1}{N}}-W-R_2}} \quad (I)$$

| EXAMPLE | R | m | K | p | L | NMR Spectrum (solvent) |
|---|---|---|---|---|---|---|
| 37 | benzocyclobutene | 1 | 4-piperidinyl | 0 | −N−CH₃ / O=C−NH−C₂H₅ | ¹H NMR (DMSO-d₆) salt 7.2 ppm, 4H, m; 6.35 ppm, 1H exchangeable; 4.35 ppm, 1H, m; 3.95 ppm, 1H, m; 3.7 to 3.0 ppm, 10H, m + dd + q + m + dd + m; 2.7 ppm, 3H, s 2.6 to 1.65 ppm, 4H m + m; 1.05 ppm, 3H, t; 10.85 ppm, 1H exchangeable. |
| 38 | benzocyclobutene | 1 | 4-piperidinyl | 0 | −N−CH₃ / O=C−NH−CH₂−C₆H₅ | ¹H NMR (CDCl₃) base 7.3 ppm, 5H, m; 7.3 to 7 ppm, 4H, m; 4.7 ppm, 1H exchangeable; 4.45 ppm, 2H, d; 4.2 ppm, 1H, m; 3.7 ppm, 1H, m; 3.4 to 3.1 ppm, 1H, dd; 3.05 ppm, 2H, d; 2.9 to 2.5 ppm, 3H, m + d + d; 2.8 ppm, 3H, s; 2.2 ppm 2H, t; 1.9 to 1.6 ppm, 4H, m |
| 39 | benzocyclobutene | 1 | 4-piperidinyl | 0 | −N−CH₃ / O=C−C=CH₂ / CH₃ | NMR (DMSO-d₆) salt 7.2 ppm, 4H, m; 5.1 ppm and 5 ppm, 2H, 2s; 3.95 ppm, 1H, m; 2.55 ppm, 3H, s; 3.7 to 3.1 ppm, 6H, 4m; 2.8 ppm, 3H, s; 2.3 ppm, 2H, m; 1.95 ppm, 3H, s; 1.75 ppm, 2H, m |
| 40 | benzocyclobutene | 1 | 4-piperidinyl | 0 | −N−CH₃ / O=C−H | NMR (CDCl₃) base 8.2 to 8.05 ppm, 1H, 2s; 7.2 ppm, 2H, m; 7.1 ppm, 2H, m; 4.3 and 3.35 ppm, 1H, 2m; 3.7 ppm, 2H, m; 3.4 ppm, 1H, dd; 3.1 ppm, 2H, m; 2.9 and 2.85 ppm, 3H, 2s; 2.8 ppm, 2H, m; 2.6 ppm, 1H, dd; 2.03 to 1.1 ppm, 6H, m |
| 41 | benzocyclobutene | 1 | 4-piperidinyl | 0 | −N−CH₃ / O=C−CH₂−O−CH₃ | NMR (DMSO d₆) salt 11.3 ppm, 1H exchanged with D₂O m; 7.3 to 7 ppm, 4H, m; 4.55 and 3.9 ppm, 1H, 2m; 4.15 et 4.05 ppm, 2H, 2s; 4 ppm, 1H, m; 3.7 to 3 ppm, 11H, m + dd + m + s + dd + m |

TABLE I-continued

COMPOUNDS OF THE GENERAL FORMULA I $$R-(CH_2)_m- \boxed{ \underset{K}{\underset{|}{N}} \overset{(CH_2)_n}{\diagup} } -(CH_2)_p- \boxed{ \underset{L}{N} \overset{R_1}{\underset{\underset{O}{\|}}{\diagdown}} C-W-R_2 } \quad (I)$$

| EXAMPLE | R | m | K | p | L | NMR Spectrum (solvent) |
|---|---|---|---|---|---|---|
| 42 | benzocyclobutenyl | 1 | 4-piperidinyl | 0 | —N—CH₃ / O=C—O—CH=CH₂ | NMR (DMSO-d₆) salt 11.05 ppm, 1H exchangeable; 7.3 to 7 ppm, 5H, 2m; 4.8 ppm, 1H, d; 4.05 ppm, 1H, dd; 4.2 ppm, 1H, m; 3.95 ppm, 1H, m 3.7 to 3 ppm, 8H, m+dd+2m+dd; 2.8 ppm, 3H, s; 2.3 ppm, 2H, m; 1.75 ppm, 2H, m |
| 43 | indanyl | 0 | 4-piperidinyl | 0 | —N—CH₃ / O=C—O—CH₂—CH(CH₃)H₃C | NMR (DMSO-d₆) salt 7.15 ppm, 4H, m; 6.6 ppm, 2H, s; 3.85 ppm, 1H, m; 3.75 ppm, 2H, d; 3.25 ppm, 1H, m; 3.15 to 2.75 ppm, 6H, m; 2.7 ppm, 3H, s; 2.2 ppm, 2H, m; 1.95 to 1.5 ppm, 5H, m; 0.9 ppm, 6H, d; 4.5 ppm, 2H, s (very level and very broad) exchangeable |
| 44 | indanyl | 0 | 4-piperidinyl | 0 | —N—CH₃ / O=C—O—CH₂—CH₂—CH₃ | NMR (CDCl₃) base 7.15 ppm, 4H, m; 4.2 to 3.8 ppm, 1H, m; 4.0 ppm, 2H, t; 3.3 to 3.0 ppm, 5H, m; 2.9 ppm, 2H, dd; 2.8 ppm, 3H, s; 2.1 ppm, 2H, m; 1.9 to 1.5 ppm, 6H, m; 0.95 ppm, 3H, t |

EXAMPLE 45

Pharmacological Study a) "Tail-Flicks" test on rats the $5HT_{1A}$ receptor antagonism of the compounds of the invention was demonstrated by the method according to Millan et al. (Neurosci, Lett, (1989), 107, p. 227-232).

Subcutaneous injection of rates with 8-OH-DPAT spontaneously induces tail movements ("Tail-Flicks"). These movements are reduced in a specific manner by $5HT_{1A}$ receptor antagonists. The $ED_{50}$ values, that is to say those amounts of the compounds of the invention that reduce 8-OH-DPTA action by 50%, are listed in Table II.

TABLE II

| COMPOUND EXAMPLE | $ED_{50}$ mg/Kg - s.c. route |
|---|---|
| 8  | 1.25 |
| 9  | 0.31 |
| 11 | 2.50 |
| 12 | 2.50 |
| 13 | 1.25 |
| 14 | 0.02 |
| 15 | 1.25 |
| 21 | 0.63 |
| 22 | 1.25 |
| 23 | 2.50 |
| 24 | 1.25 |
| 28 | 2.50 |
| 31 | 0.31 |
| 42 | 1.25 |
| 44 | 2.5 | b) Sigma binding test (in vitro)

The affinity of the compounds of the invention to the sigma receptor in brain tissue is evaluated by the degree of inhibition of the binding of a sigma site radioligand in in vitro competition experiments.

The experiment protocol used in that described by WEBER et al. Proc. Nat. Acad. Sci. USA, (1986), 83, 8784-8788.

The ligand is 1,3-di-(2-[5-$^3$H]tolyl)guanidine (Dupont de Nemours—55 Ci/mmol) at a final concentration of 2 nM.

The membrane preparation is a suspension of central nervous system microsomes of a guinea pig used at a final concentration of 0.5 mg of prot/ml.

The non-specific fixation is determined in the presence of 10 μM of haloperidol.

The results, given in Table III, to illustrate the invention are expressed as $IC_{50} = K.0.5$ (M)

TABLE III

| Inhibition of [3H] ditolylguanidine binding | |
|---|---|
| COMPOUND EXAMPLE | $IC_{50}$ in M |
| 9  | $3.10^{-8}$ |
| 12 | $3.10^{-8}$ |
| 15 | $1.10^{-7}$ |
| 18 | $8.10^{-8}$ |
| 19 | $3.10^{-8}$ |
| 24 | $2.10^{-8}$ |
| 31 | $2.10^{-7}$ |
| 42 | $5.10^{-8}$ |
| 43 | $4.10^{-9}$ |
| 44 | $4.10^{-8}$ |

EXAMPLE 46

Pharmaceutical Composition

Tablets each containing 5 mg of propyl N-[1-(benzocyclobuten-1-ylmethyl)-piperid-4-yl]-N-methylcarbamate hydrochloride (P.B.M.P.C.)

| | |
|---|---|
| P.B.M.P.M.C. | 5 g |
| wheat starch | 100 g |
| cornstarch | 20 g |
| magnesium stearate | 20 g |
| talc | 20 g | for 1000 tablets each containing 5 mg of active ingredient.

We claim:

1. A compound selected from the hose of formula I $$R-(CH_2)_m-N\underset{}{\overset{(CH_2)_n}{\diagup\diagdown}}(CH_2)_p-N\underset{\underset{O}{\overset{\|}{C}-W-R_2}}{\overset{R_1}{\diagdown}} \quad (I)$$

in which:
m represents zero, 1, 2, 3 or 4,
n represents 1 and p represent zero, 1 or 2,
W represents oxygen, —NH—, or a single bond,
R represents:
benzocyclobuten-1-yl of formula B:

(B)

or indanyl of formula C:

(C)

in which:
$R_7$, $R_8$ and $R_9$, which may be the same or different, each represents hydrogen, halogen, ($C_1$-$C_6$) -alkyl or -alkoxy, polyhalogenated ($C_1$-$C_6$) alkyl, or hydroxy, or when R represents B, $R_7$ and $R_8$ or $R_8$ and $R_9$ together also may form methylenedioxy, ethylenedioxy, a furan ring, or a dihydrofuran ring when R represents (B), and have the same meanings less ($C_1$-$C_6$)-alkoxy when R represents (C), and $R_{10}$ represents hydrogen or ($C_1$-$C_6$) alkyl;
$R_1$ represents hydrogen or ($C_1$-$C_6$) alkyl, or carbocylic aryl, with the proviso, however, that when, simultaneously, R represents indanyl, p represents zero and W represents a single bond, R1 does not represent aryl;
$R_2$ represents hydrogen, ($C_1$-$C_6$) alkyl, ($C_2$-$C_6$) alkenyl, ($C_4$-$C_7$) cycloalkyl, benzyl or phenyl (each optionally substituted by one or more halogen, hydroxy, ($C_1$–$C_6$)-alkyl or -alkoxy, ($C_7$–$C_{12}$) aralkyl, ($C_2$–$C_7$) alkoxyalkyl or polyhalogenated ($C_1$–$C_6$) alkyl, the optical isomers thereof and the addition salts thereof with a pharmaceutically acceptable organic or mineral acid.

2. A compound of claim 1 which is:

N-(1-indan-2-ylpiperid-4-yl)-N-methylpropionamide, the optical isomers thereof and the addition salts thereof with a pharmaceutically acceptable organic or mineral acid.

3. A compound of claim 1 which is:

propyl N-[1-(benzocyclobuten-1-ylmethyl)-piperid-4-yl]-N-methylcarbamate, the optical isomers thereof and the addition salts thereof with a pharmaceutically acceptable organic or mineral acid.

4. A compound of claim 1 which is:

methyl N-[1-(benzocyclobuten-1-ylmethyl)-piperid-4-yl]-N-ethylcarbamate, the optical isomers thereof and the addition salts thereof with a pharmaceutically acceptable organic or mineral acid.

5. A compound of claim 1 which is:

N-[1-(benzocyclobuten-1-ylmethyl)-piperid-4-yl]-N-ethylacetamide, the optical isomers thereof and the addition salts thereof with a pharmaceutically acceptable organic or mineral acid.

6. A compound of claim 1 which is:

N-[1-(benzocyclobuten-1-ylmethyl)-piperid-4-yl]-N-methylbutyramide, the optical isomers thereof and the addition salts thereof with a pharmaceutically acceptable organic or mineral acid.

7. A compound of claim 1 which is:

methyl N-[1-(benzocyclobuten-1-ylmethyl)piperid-4-yl]-N-methylcarbamate, the optical isomers thereof and the addition salts thereof with a pharmaceutically acceptable organic or mineral acid.

8. A compound of claim 1 which is:

ethyl N-[1-(benzocyclobuten-1-ylmethyl)-piperid-4-yl]-N-ethylcarbamate, the optical isomers thereof and the addition salts thereof with a pharmaceutically acceptable organic or mineral acid.

9. A compound of claim 1 which is:

phenyl N-[1-(benzocyclobuten-1-ylmethyl)-piperid-4-yl]-N-methylcarbamate, the optical isomers thereof and the addition salts thereof with a pharmaceutically acceptable organic or mineral acid.

10. A compound of claim 1 which is:

benzyl N-[1-(benzocyclobuten-1-ylmethyl)-piperid-4-yl]-N-methylcarbamate, the optical isomers thereof and the addition salts thereof with a pharmaceutically acceptable organic or mineral acid.

11. A compound of claim 1 which is:

vinyl N-[1-(benzocyclobuten-1-ylmethyl)-piperid-4-yl]-N-methylcarbamate, the optical isomers thereof and the addition salts thereof with a pharmaceutically acceptable organic or mineral acid.

12. A compound of claim 1 which is:

isobutyl N-[1-(inden-2-yl)-piperid-4-yl]-N-methylcarbamate, the optical isomers thereof and the addition salts thereof with a pharmaceutically acceptable organic or mineral acid.

13. A compound of claim 1 which is:

propyl N-[1-indan-2-yl)-piperid-4-yl]-N-methylcarbamate, the optical isomers thereof and the addition salts thereof with a pharmaceutically acceptable organic or mineral acid.

14. A method for treating a living animal body afflicted with a disease resulting from pain, stress, migraine, anxiety, depression and schizophrenia, comprising the step of administering an amount of a compound of claim 1 which is suitable for the alleviation of the said condition.

15. A pharmaceutical composition containing as active ingredient an effective amount of a compound of claim 1, alone or in combination with one or more physiologically tolerable inert carriers.

* * * * *

UNITED STATES PATENT AND TRADEMARK OFFICE
CERTIFICATE OF CORRECTION

PATENT NO. : 5,189,045  
DATED : Feb. 23, 1993  
INVENTOR(S) : Jean-Louis Peglion, Francis Colpaert Page 1 of 3

It is certified that error appears in the above-indentified patent and that said Letters Patent is hereby corrected as shown below:

Title Page, second column, [57] ABSTRACT, line 8; "radical, or" should read -- radical or --.

Title Page, second column, [57] ABSTRACT, line 9; cancel "a 2,3-dihydrobenzofuran- 2,yl".
   line 1,2)
Column 4, line 4; "Rd/C," should read -- Pd/C, --.
Column 4, line 15; "p,g and" should read -- p, q and --.
Column 6, line 16; "defined formula" should read -- defined for formula --.
Column 8, line 20; "-4-yl)-" should read -- -4-yl} - --.
Column 8, approximately line 53; "the" should read -- The --.
Column 9, line 3; "p + s + m + gl + H" should read
   -- m + s + m + q + 1H --.
Column 9, approximately line 20; "N-(1-" should read --N-{1- --.
Column 9, approximately line 20/21; "4-yl)-" should read --4-yl} - --.
Column 9, line 54; "The" should read -- This --.
Column 9, approximately line 62; "2T;" should read -- 2t; --.
Column 10, line 1; "(4-oxo-4H-chromen-2) should read
   -- (4-oxo-4H-chromen-2-yl) --.
Column 10, approximately line 53; "N-{(1-[2-(4-oxo-" should read -- N-{1-[2-(4-oxo- --.
Column 10, line 64; "mg" should read -- mm --.
Column 11, line 45; "N-[1-" should read -- N-{1- --.
Column 12, approximately line 11; "N-(1-" should read --N-{1- --.
Column 12, line 19; "-4-yl)-" should read -- -- -4-yl} - --.
Column 12, line 64; "7%" should read -- 71% --.
Column 14, line 49; "5°" should read -- 50° --.
Column 16, line 36/37; "hydroxylamide" should read --hydroxylamine--.
Column 18, line 60/61; "hydro-chloride" should read -- hydro-chloric --.
Column 20, approximately line 8; "-4-yl)" should read -- -4-yl] --.
Column 20, line 15; "203°" should read -- 302° --.
Column 22, line 3; "-methyl)-" should read -- -methyl} - --.

UNITED STATES PATENT AND TRADEMARK OFFICE
CERTIFICATE OF CORRECTION

PATENT NO. : 5,189,045

DATED : Feb. 23, 1993

INVENTOR(S) : Jean-Louis Peglion, Francis Colpaert

Page 2 of 3

It is certified that error appears in the above-indentified patent and that said Letters Patent is hereby corrected as shown below:

Column 22, approximately line 16; "2H, 2.8" should read
-- 2H, m; 2.8 --.
Column 22, line 64; "(benzyocyclobuten" should read
-- (benzocyclobuten --.
Column 23, approximately line 14; "N-{(1-" should read
-- N-{1- --.
Column 23, approximately line 15; "-4-yl)-" should read
-- -4-yl} - --.
Column 24, line 5; "2H, g;" should read -- 2H, q; --.
Column 24, line 19; "N-[1" should read -- N-{1 --.
Column 24, line 20; "-4-yl)" should read -- -4-yl} - --.
Column 27, line 15; "N-{ (1-" should read -- N-{ [1- --.
Col. 27, line 21,      -4-yln-" should read -- -4-yl-N- --.
Column 30, approximately line 17; "-4-yl)-" should read
-- -4-yl} - --.
Column 33, line 53; "N-[1-benzyocy-" should read
--N-[1-(benzocy--

Column 37/38, TABLE I-continued, EXAMPLE 6, last column, line 5;
  "g;" should read -- q; --.
Column 39/40, TABLE I-continued, EXAMPLE 9, last column, line 3;
  delete "4H,m 4.4 ppm, 1H, m;" to read --3H, m+t; 3.9 to 3.3 ppm,--.
Column 45/46, TABLE I-continued, EXAMPLE 23, last column, line
  5/6, after "1H, and before "dd" insert-- d; 3.1 ppm, 1H, --.
Column 47/48, TABLE I-continued, EXAMPLE 27, last column,
  5th line; "2s;" should read -- 2m; --.
Column 47/48, TABLE I-continued, EXAMPLE 28, last column,line 3,4;
  delete "2H, s; 6.7 ppm, 1H, s; 6.7 ppm, 1H, d; 6.55 ppm,".
Column 47/48, TABLE I-continued, EXAMPLE 28, last column, 2nd
  line from the end; insert "m;" at the beginning of the line
  after "2H,".
Column 49/50, TABLE I-continued, EXAMPLE 30, last column, 2nd
line; "1H,d;" should read -- 1H, dd; --.

UNITED STATES PATENT AND TRADEMARK OFFICE
CERTIFICATE OF CORRECTION

PATENT NO. : 5,189,045
DATED : Feb. 23, 1993
INVENTOR(S) : Jean-Louis Peglion, Francis Colpaert It is certified that error appears in the above-indentified patent and that said Letters Patent is hereby corrected as shown below:

```
Column 55/56, TABLE I-continued, Example 42, last column, 5th line;
   "m 3.7" should read -- m; 3.7 --.
Column 57, line 10; "rates" should read  -- rats --.
Column 57, line 41; "in" should read -- is --.
Column 58, approximately line 18; "from the hose" should read
   -- from those --.
Column 59, line 5/6; "pharmaceutically acceptable" should read
   -- pharmaceutically-acceptable --.
```

Signed and Sealed this

First Day of March, 1994

Attest:

BRUCE LEHMAN

*Attesting Officer*        *Commissioner of Patents and Trademarks*